(12) United States Patent
Komori et al.

(10) Patent No.: US 6,403,534 B1
(45) Date of Patent: Jun. 11, 2002

(54) URACIL COMPOUNDS AND USE THEREOF

(75) Inventors: Takashi Komori, Toyonaka; Yuzuru Sanemitsu, Kobe, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/892,475

(22) Filed: Jun. 28, 2001

(30) Foreign Application Priority Data

Jun. 28, 2000 (JP) ......................................... 2000-194272

(51) Int. Cl.$^7$ ...................... C07D 239/54; A01N 43/54
(52) U.S. Cl. .................. 504/243; 544/312; 544/314
(58) Field of Search .................. 504/243; 544/312, 544/314

(56) References Cited

U.S. PATENT DOCUMENTS

| | | | |
|---|---|---|---|
| 4,859,229 A | 8/1989 | Wenger et al. | 544/314 |
| 5,981,436 A | 11/1999 | Drewes et al. | 504/243 |

FOREIGN PATENT DOCUMENTS

| | | |
|---|---|---|
| CA | 2227762 | 2/1997 |
| DE | 19604229 | 8/1996 |
| WO | 9532952 | 12/1995 |
| WO | 9701541 | 1/1997 |

*Primary Examiner*—John M. Ford
(74) *Attorney, Agent, or Firm*—Birch, Stewart, Kolasch & Birch, LLP

(57) ABSTRACT

The present invention provides an uracil compound of the formula:

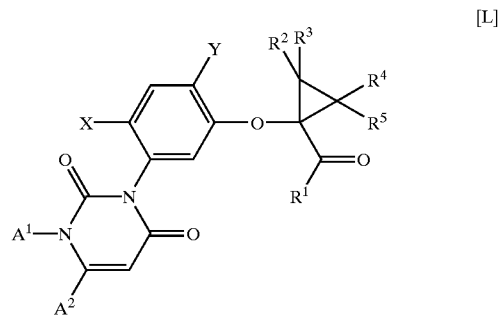

[L]

wherein $A^1$ represents amino or $C_1$–$C_3$ alkyl, $A^2$ represents $C_1$–$C_3$ haloalkyl, X represents hydrogen or halogen, Y represents halogen, $R^1$ represents —$OR^{21}$, —$ON(R^{22})R^{23}$, —$ON=C(R^{24})R^{25}$, —$SR^{26}$, —$N(R^{27})R^{28}$, —$N(R^{29})OR^{30}$, —$N(R^{31})SO_2R^{32}$ or —$N(R^{33})N(R^{34})R^{35}$, and $R^2$, $R^3$, $R^4$ and $R^5$ independently represent hydrogen or $C_1$–$C_3$ alkyl and a herbicidal composition comprising the above uracil compound as an active ingredient. The uracil compound has excellent herbicidal activity.

11 Claims, No Drawings

URACIL COMPOUNDS AND USE THEREOF

BACKGROUND OF THE INVENTION

1. Field of the Invention

The present invention relates to uracil compounds and herbicidal compositions comprising them as active ingredients.

2. Description of Related Art

Although numerous herbicides have been commercialized, the weeds that need to be controlled are varied and their germination lasts over a long period. Accordingly, new herbicides are needed that have a higher herbicidal activity and a wide herbicidal spectrum but do not cause phytotoxicity on crops.

U.S. Pat. No. 4,859,229 and WO 95/32952 disclose that certain kinds of phenyluracil compounds have an herbicidal activity. However, uracil compounds having improved herbicidal performance are desired.

The purpose of the invention is to provide compounds having excellent performance as a herbicide.

SUMMARY OF THE INVENTION

As the result of extensive studies seeking compounds having excellent performance as a herbicide, the present inventors have found that uracil compounds represented by the following formula [L] have an excellent performance as a herbicide and have completed the invention. Accordingly, the invention provides uracil compounds (hereinafter, referred to as the present compound) represented by the formula [L]:

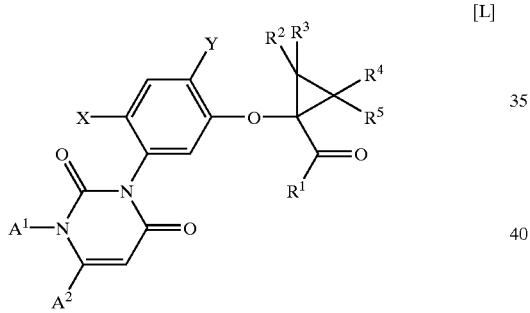

wherein $A^1$ represents amino or $C_1$–$C_3$ alkyl, $A^2$ represents $C_1$–$C_3$ haloalkyl, X represents hydrogen or halogen, Y represents halogen, $R^1$ represents —$OR^{21}$, —$ON(R^{22})R^{23}$, —$ON=C(R^{24})R^{25}$, —$SR^{26}$, —$N(R^{27})R^{28}$, —$N(R^{29})OR^{30}$, —$N(R^{31})SO_2R^{32}$ or —$N(R^{33})N(R^{34})R^{35}$, (wherein $R^{21}$ represents hydrogen, $C_1$–$C_6$ alkyl, $C_1$–$C_6$ haloalkyl, $C_3$–$C_6$ alkenyl, $C_3$–$C_6$ alkynyl, $C_3$–$C_6$ cycloalkyl, carboxy $C_1$–$C_6$ alkyl, $C_1$–$C_6$ alkoxycarbonyl $C_1$–$C_6$ alkyl, $C_3$–$C_6$ alkenyloxycarbonyl $C_1$–$C_6$ alkyl, $C_3$–$C_6$ alkynyloxycarbonyl $C_1$–$C_6$ alkyl, $C_1$–$C_6$ alkoxy $C_1$–$C_6$ alkyl, benzyl or phenyl (the benzyl and phenyl maybe substituted with one or more of halogen, $C_1$–$C_6$ alkyl and $C_1$–$C_6$ alkoxy) or tetrahydrofuryl (the tetrahydrofuryl may be substituted with one or more of hydroxy, $C_1$–$C_6$ alkoxy, $C_3$–$C_6$ alkenyloxy, $C_3$–$C_6$ alkynyloxy and $C_1$–$C_6$ alkylcarbonyloxy), $R^{22}$ and $R^{23}$ independently represent hydrogen, $C_1$–$C_6$ alkyl, $C_1$–$C_6$ haloalkyl, $C_3$–$C_6$ alkenyl, $C_3$–$C_6$ alkynyl or benzyl (the benzyl may be substituted with one or more of halogen, $C_1$–$C_6$ alkyl and $C_1$–$C_6$ alkoxy), $R^{24}$ and $R^{25}$ independently represent hydrogen, $C_1$–$C_6$ alkyl, $C_1$–$C_6$ haloalkyl, $C_3$–$C_6$ alkenyl, $C_3$–$C_6$ alkynyl, benzyl or phenyl (the benzyl and phenyl may be substituted with one or more of halogen, $C_1$–$C_6$ alkyl and $C_1$–$C_6$ alkoxy), $R^{26}$ represents hydrogen, $C_1$–$C_6$ alkyl, $C_1$–$C_6$ haloalkyl, $C_3$–$C_6$ alkenyl, $C_3$–$C_6$ alkynyl, $C_3$–$C_6$ cycloalkyl, carboxy $C_1$–$C_6$ alkyl, $C_1$–$C_6$ alkoxycarbonyl $C_1$–$C_6$ alkyl, $C_3$–$C_6$ alkenyloxycarbonyl $C_1$–$C_6$ alkyl, $C_3$–$C_6$ alkynyloxycarbonyl $C_1$–$C_6$ alkyl, $C_1$–$C_6$ alkoxy $C_1$–$C_6$ alkyl, benzyl or phenyl (the benzyl and phenyl maybe substituted with one or more of halogen, $C_1$–$C_6$ alkyl and $C_1$–$C_6$ alkoxy), $R^{27}$ represents hydrogen, $C_1$–$C_6$ alkyl, $C_1$–$C_6$ haloalkyl, $C_3$–$C_6$ alkenyl, $C_3$–$C_6$ alkynyl, $C_3$–$C_6$ cycloalkyl, carboxy $C_1$–$C_6$ alkyl, $C_1$–$C_6$ alkoxycarbonyl $C_1$–$C_6$ alkyl, $C_3$–$C_6$ alkenyloxycarbonyl $C_1$–$C_6$ alkyl, $C_3$–$C_6$ alkynyloxycarbonyl $C_1$–$C_6$ alkyl, $C_1$–$C_6$ alkoxy $C_1$–$C_6$ alkyl, benzyl or phenyl (the benzyl and phenyl maybe substituted with one or more of halogen, $C_1$–$C_6$ alkyl and $C_1$–$C_6$ alkoxy), $R^{28}$ represents hydrogen, $C_1$–$C_6$ alkyl, $C_1$–$C_6$ haloalkyl, $C_3$–$C_6$ alkenyl, $C_3$–$C_6$ alkynyl, benzyl or phenyl (the benzyl and phenyl may be substituted with one or more of halogen, $C_1$–$C_6$ alkyl and $C_1$–$C_6$ alkoxy), $R^{29}$ and $R^{30}$ independently represent hydrogen, $C_1$–$C_6$ alkyl, $C_1$–$C_6$ haloalkyl, $C_3$–$C_6$ alkenyl, $C_3$–$C_6$ alkynyl or benzyl (the benzyl may be substituted with one or more of halogen, $C_1$–$C_6$ alkyl and $C_1$–$C_6$ alkoxy), $R^{31}$ represents hydrogen, $C_1$–$C_6$ alkyl, $C_1$–$C_6$ haloalkyl, $C_3$–$C_6$ alkenyl, $C_3$–$C_6$ alkynyl, benzyl or phenyl (the benzyl and phenyl may be substituted with one or more of halogen, $C_1$–$C_6$ alkyl and $C_1$–$C_6$ alkoxy), $R^{32}$ represents $C_1$–$C_6$ alkyl, $C_1$–$C_6$ haloalkyl, $C_3$–$C_6$ alkenyl, $C_3$–$C_6$ alkynyl, benzyl or phenyl (the benzyl and phenyl may be substituted with one or more of halogen, $C_1$–$C_6$ alkyl and $C_1$–$C_6$ alkoxy), $R^{33}$, $R^{34}$ and $R^{35}$ independently represent hydrogen, $C_1$–$C_6$ alkyl, $C_1$–$C_6$ haloalkyl, $C_3$–$C_6$ alkenyl, $C_3$–$C_6$ alkynyl, benzyl or phenyl (the benzyl and phenyl may be substituted with one or more of halogen, $C_1$–$C_6$ alkyl and $C_1$–$C_6$ alkoxy), $R^2$, $R^3$, $R^4$ and $R^5$ independently represent hydrogen or $C_1$–$C_3$ alkyl.

The present invention also provides a herbicidal composition comprising, as an active ingredient, such an uracil compound.

DETAILED DESCRIPTION OF THE INVENTION

In the present invention, stereoisomers of the uracil compounds may exist with respect to a double bond or an asymmetric carbon atom. It will be appreciated that the present invention includes individual stereoisomers of the uracil compounds, as well as mixtures thereof.

In the present invention:

With regard to $A^1$, $C_1$–$C_3$ alkyl represents methyl, ethyl, propyl or isopropyl.

With regard to $A^2$, $C_1$–$C_3$ haloalkyl includes trifluoromethyl, difluoromethyl, fluoromethyl, chlorodifluoromethyl, dichlorofluoromethyl, trichloromethyl, pentafluoroethyl, 2,2,2-trifluoroethyl, 1,1-difluoroethyl, 1-fluoroethyl, 2-fluoroethyl and the like.

With regard to $R^2$, $R^3$, $R^4$ and $R^5$, $C_1$–$C_3$ alkyl represents methyl, ethyl, propyl or isopropyl.

With regard to $R^{21}$, $C_1$–$C_6$ alkyl includes methyl, ethyl, propyl, isopropyl, butyl, isobutyl, t-butyl (hereinafter "t" means "tertiary", unless noted otherwise), pentyl, isopentyl, neopentyl, hexyl and the like;

$C_1$–$C_6$ haloalkyl includes fluoromethyl, chloromethyl, bromomethyl, trifluoromethyl, chloroethyl and the like;

$C_3$–$C_6$ alkenyl includes allyl, 1-methyl-2-propenyl, 2-methyl-2-propenyl, 2-butenyl, 3-butenyl and the like;

$C_3$–$C_6$ alkynyl includes propargyl, 1-methyl-2-propynyl, 1,1-dimethyl-2-propynyl, 2-butynyl, 3-butynyl and the like;

$C_3$–$C_6$ cycloalkyl includes cyclopropyl, cyclobutyl, cyclopentyl, cyclohexyl and the like;

carboxy $C_1$–$C_6$ alkyl includes carboxymethyl, 1-carboxyethyl, 1-carboxy-1-methylethyl and the like;

$C_1$–$C_6$ alkoxycarbonyl $C_1$–$C_6$ alkyl includes methoxycarbonylmethyl, ethoxycarbonylmethyl, 1-methoxycarbonylethyl, 1-methoxycarbonyl-1-methylethyl, 1-ethoxycarbonylethyl and the like;

$C_3$–$C_6$ alkenyloxycarbonyl $C_1$–$C_6$ alkyl includes allyloxycarbonylmethyl, 1-allyloxycarbonylethyl, 2-allyloxycarbonylethyl, 1-allyloxycarbonyl-1-methylethyl and the like;

$C_3$–$C_6$ alkynyloxycarbonyl $C_1$–$C_6$ alkyl includes propargyloxycarbonylmethyl, 1-propargyloxycarbonylethyl, 2-propargyloxycarbonylethyl, 1propargyloxycarbonyl-1-methylethyl and the like;

$C_1$–$C_6$ alkoxy $C_1$–$C_6$ alkyl includes 2-methoxyethyl, 2-ethoxyethyl, 3-methoxypropyl and the like;

benzyl which may be substituted with one or more of halogen, $C_1$–$C_6$ alkyl and $C_1$–$C_6$ alkoxy includes benzyl, 4-chlorobenzyl, 4-methylbenzyl and the like;

phenyl which may be substituted with one or more of halogen, $C_1$–$C_6$ alkyl and $C_1$–$C_6$ alkoxy includes phenyl, 4-chlorophenyl, p-tolyl, o-tolyl and the like; and tetrahydrofuryl which may be substituted with one or more of hydroxy, $C_1$–$C_6$ alkoxy, $C_3$–$C_6$ alkenyloxy, $C_3$–$C_6$ alkynyloxy and $C_1$–$C_6$ alkylcarbonyloxy includes 3-tetrahydrofuryl, 4-hydroxy-3-tetrahydrofuryl, 4-methoxy-3-tetrahydrofuryl, 4-acetoxy-3-tetrahydrofuryl and the like.

With regard to $R^{22}$ and $R^{23}$, $C_1$–$C_6$ alkyl includes methyl, ethyl, propyl, isopropyl, butyl, isobutyl, t-butyl, pentyl, isopentyl, neopentyl, hexyl and the like;

$C_1$–$C_6$ haloalkyl includes fluoromethyl, chloromethyl, bromomethyl, trifluoromethyl, chloroethyl and the like;

$C_3$–$C_6$ alkenyl includes allyl, 1-methyl-2-propenyl, 2-methyl-2-propenyl, 2-butenyl, 3-butenyl and the like;

$C_3$–$C_6$ alkynyl includes propargyl, 1-methyl-2-propynyl, 1,1-dimethyl-2-propynyl, 2-butynyl, 3-butynyl and the like; and benzyl which may be substituted with one or more of halogen, $C_1$–$C_6$ alkyl and $C_1$–$C_6$ alkoxy includes benzyl, 4-chlorobenzyl, 4-methylbenzyl and the like.

With regard to $R^{24}$ and $R^{25}$, $C_1$–$C_6$ alkyl includes methyl, ethyl, propyl, isopropyl, butyl, isobutyl, t-butyl, pentyl, isopentyl, neopentyl, hexyl and the like;

$C_1$–$C_6$ haloalkyl includes fluoromethyl, chloromethyl, bromomethyl, trifluoromethyl, chloroethyl and the like;

$C_3$–$C_6$ alkenyl includes allyl, 1-methyl-2-propenyl, 2-methyl-2-propenyl, 2-butenyl, 3-butenyl and the like;

$C_3$–$C_6$ alkynyl includes propargyl, 1-methyl-2-propynyl, 1,1-dimethyl-2-propynyl, 2-butynyl, 3-butynyl and the like;

benzyl which may be substituted with one or more of halogen, $C_1$–$C_6$ alkyl and $C_1$–$C_6$ alkoxy includes benzyl, 4-chlorobenzyl, 4-methylbenzyl and the like; and phenyl which may be substituted with one or more of halogen, $C_1$–$C_6$ alkyl and $C_1$–$C_6$ alkoxy includes phenyl, 4-chlorophenyl, p-tolyl, o-tolyl and the like.

With regard to $R^{26}$, $C_1$–$C_6$ alkyl includes methyl, ethyl, propyl, isopropyl, butyl, isobutyl, t-butyl, pentyl, isopentyl, neopentyl, hexyl and the like;

$C_1$–$C_6$ haloalkyl includes fluoromethyl, chloromethyl, bromomethyl, trifluoromethyl, chloroethyl and the like;

$C_3$–$C_6$ alkenyl includes allyl, 1-methyl-2-propenyl, 2-methyl-2-propenyl, 2-butenyl, 3-butenyl and the like;

$C_3$–$C_6$ alkynyl includes propargyl, 1-methyl-2-propynyl, 1,1-dimethyl-2-propynyl, 2-butynyl, 3-butynyl and the like;

$C_3$–$C_6$ cycloalkyl includes cyclopropyl, cyclobutyl, cyclopentyl, cyclohexyl and the like;

carboxy $C_1$–$C_6$ alkyl includes carboxymethyl, 1-carboxyethyl, 1-carboxy-1-methylethyl and the like;

$C_1$–$C_6$ alkoxycarbonyl $C_1$–$C_6$ alkyl includes methoxycarbonylmethyl, ethoxycarbonylmethyl, 1-methoxycarbonylethyl, 1-methoxycarbonyl-1-methylethyl, 1-ethoxycarbaonylethyl and the like;

$C_3$–$C_6$ alkenyloxycarbonyl $C_1$–$C_6$ alkyl includes allyloxycarbonylmethyl, 1-allyloxycarbonylethyl, 2-allyloxycarbonylethyl, 1-allyloxycarbonyl-1-methylethyl and the like;

$C_3$–$C_6$ alkynyloxycarbonyl $C_1$–$C_6$ alkyl includes propargyloxycarbonylmethyl, 1-propargyloxycarbonylethyl, 2-propargyloxycarbonylethyl, 1-propargyloxycarbonyl-1-methylethyl and the like;

$C_1$–$C_6$ alkoxy $C_1$–$C_6$ alkyl includes 2-methoxyethyl, 2-ethoxyethyl, 3-methoxypropyl and the like;

benzyl which may be substituted with one or more of halogen, $C_1$–$C_6$ alkyl and $C_1$–$C_6$ alkoxy includes benzyl, 4-chlorobenzyl, 4-methylbenzyl and the like; and phenyl which may be substituted with one or more of halogen, $C_1$–$C_6$ alkyl and $C_1$–$C_6$ alkoxy includes phenyl, 4-chlorophenyl, p-tolyl, o-tolyl and the like.

With regard to $R^{27}$, $C_1$–$C_6$ alkyl includes methyl, ethyl, propyl, isopropyl, butyl, isobutyl, t-butyl, pentyl, isopentyl, neopentyl, hexyl and the like;

$C_1$–$C_6$ haloalkyl includes fluoromethyl, chloromethyl, bromomethyl, trifluoromethyl, chloroethyl and the like;

$C_3$–$C_6$ alkenyl includes allyl, 1-methyl-2-propenyl, 2-methyl-2-propenyl, 2-butenyl, 3-butenyl and the like;

$C_3$–$C_6$ alkynyl includes propargyl, 1-methyl-2-propynyl, 1,1-dimethyl-2-propynyl, 2-butynyl, 3-butynyl and the like;

$C_3$–$C_6$ cycloalkyl includes cyclopropyl, cyclobutyl, cyclopentyl, cyclohexyl and the like;

carboxy $C_1$–$C_6$ alkyl includes carboxymethyl, 1-carboxyethyl, 1-carboxy-1-methylethyl and the like;

$C_1$–$C_6$ alkoxycarbonyl $C_1$–$C_6$ alkyl includes methoxycarbonylmethyl, ethoxycarbonylmethyl, 1-methoxycarbonylethyl, 1-methoxycarbonyl-1-methylethyl, 1-ethoxycarbonylethyl and the like;

$C_3$–$C_6$ alkenyloxycarbonyl $C_1$–$C_6$ alkyl includes allyloxycarbonylmethyl, 1-allyloxycarbonylethyl, 2-allyloxycarbonylethyl, 1-allyloxycarbonyl-1-methylethyl and the like;

$C_3$–$C_6$ alkynyloxycarbonyl $C_1C_6$ alkyl includes propargyloxycarbonylmethyl, 1-propargyloxycarbonylethyl, 2-propargyloxycarbonylethyl, 1-propargyloxycarbonyl-1-methylethyl and the like;

$C_1$–$C_6$ alkoxy $C_1$–$C_6$ alkyl includes 2-methoxyethyl, 2-ethoxyethyl, 3-methoxypropyl and the like;

benzyl which may be substituted with one or more of halogen, $C_1$–$C_6$ alkyl and $C_1$–$C_6$ alkoxy includes benzyl, 4-chlorobenzyl, 4-methylbenzyl and the like; and phenyl which may be substituted with one or more of halogen, $C_1$–$C_6$ alkyl and $C_1$–$C_6$ alkoxy includes phenyl, 4-chlorophenyl, p-tolyl, o-tolyl and the like.

With regard to $R^{28}$, $C_1$–$C_6$ alkyl includes methyl, ethyl, propyl, isopropyl, butyl, isobutyl, t-butyl, pentyl, isopentyl, neopentyl, hexyl and the like;

$C_1$–$C_6$ haloalkyl includes fluoromethyl, chloromethyl, bromomethyl, trifluoromethyl, chloroethyl and the like;

$C_3$–$C_6$ alkenyl includes allyl, 1-methyl-2-propenyl, 2-methyl-2-propenyl, 2-butenyl, 3-butenyl and the like;

$C_3$–$C_6$ alkynyl includes propargyl, 1-methyl-2-propynyl, 1,1-dimethyl-2-propynyl, 2-butynyl, 3-butynyl and the like;

benzyl which may be substituted with one or more of halogen, $C_1$–$C_6$ alkyl and $C_1$–$C_6$ alkoxy includes benzyl, 4-chlorobenzyl, 4-methylbenzyl and the like; and phenyl which may be substituted with one or more of halogen, $C_1$–$C_6$ alkyl and $C_1$–$C_6$ alkoxy includes phenyl, 4-chlorophenyl, p-tolyl, o-tolyl and the like.

With regard to $R^{29}$ and $R^{30}$, $C_1$–$C_6$ alkyl includes methyl, ethyl, propyl, isopropyl, butyl, isobutyl, t-butyl, pentyl, isopentyl, neopentyl, hexyl and the like;

$C_1$–$C_6$ haloalkyl includes fluoromethyl, chloromethyl, bromomethyl, trifluoromethyl, chloroethyl and the like;

$C_3$–$C_6$ alkenyl includes allyl, 1-methyl-2-propenyl, 2-methyl-2-propenyl, 2-butenyl, 3-butenyl and the like;

$C_3$–$C_6$ alkynyl includes propargyl, 1-methyl-2-propynyl, 1,1-dimethyl-2-propynyl, 2-butynyl, 3-butynyl and the like; and benzyl which may be substituted with one or more of halogen, $C_1$–$C_6$ alkyl and $C_1$–$C_6$ alkoxy includes benzyl, 4-chlorobenzyl, 4-methylbenzyl and the like.

With regard to $R^{31}$, $C_1$–$C_6$ alkyl includes methyl, ethyl, propyl, isopropyl, butyl, isobutyl, t-butyl, pentyl, isopentyl, neopentyl, hexyl and the like;

$C_1$–$C_6$ haloalkyl includes fluoromethyl, chloromethyl, bromomethyl, trifluoromethyl, chloroethyl and the like;

$C_3$–$C_6$ alkenyl includes allyl, 1-methyl-2-propenyl, 2-methyl-2-propenyl, 2-butenyl, 3-butenyl and the like;

$C_3$–$C_6$ alkynyl includes propargyl, 1-methyl-2-propynyl, 1,1-dimethyl-2-propynyl, 2-butynyl, 3-butynyl and the like;

benzyl which may be substituted with one or more of halogen, $C_1$–$C_6$ alkyl and $C_1$–$C_6$ alkoxy includes benzyl, 4-chlorobenzyl, 4-methylbenzyl and the like; and phenyl which may be substituted with one or more of halogen, $C_1$–$C_6$ alkyl and $C_1$–$C_6$ alkoxy includes phenyl, 4-chlorophenyl, p-tolyl, o-tolyl and the like.

With regard to $R^{32}$, $C_1$–$C_6$ alkyl includes methyl, ethyl, propyl, isopropyl, butyl, isobutyl, t-butyl, pentyl, isopentyl, neopentyl, hexyl and the like;

$C_1$–$C_6$ haloalkyl includes fluoromethyl, chloromethyl, bromomethyl, trifluoromethyl, chloroethyl and the like;

$C_3$–$C_6$ alkenyl includes allyl, 1-methyl-2-propenyl, 2-methyl-2-propenyl, 2-butenyl, 3-butenyl and the like;

$C_3$–$C_6$ alkynyl includes propargyl, 1-methyl-2-propynyl, 1,1-dimethyl-2-propynyl, 2-butynyl, 3-butynyl and the like;

benzyl which may be substituted with one or more of halogen, $C_1$–$C_6$ alkyl and $C_1$–$C_6$ alkoxy includes benzyl, 4-chlorobenzyl, 4-methylbenzyl and the like; and phenyl which may be substituted with one or more of halogen, $C_1$–$C_6$ alkyl and $C_1$–$C_6$ alkoxy includes phenyl, 4-chlorophenyl, p-tolyl, o-tolyl and the like.

With regard to $R^{33}$, $R^{34}$ and $R^{35}$, $C_1$–$C_6$ alkyl includes methyl, ethyl, propyl, isopropyl, butyl, isobutyl, t-butyl, pentyl, isopentyl, neopentyl, hexyl and the like;

$C_1$–$C_6$ haloalkyl includes fluoromethyl, chloromethyl, bromomethyl, trifluoromethyl, chloroethyl and the like;

$C_3$–$C_6$ alkenyl includes allyl, 1-methyl-2-propenyl, 2-methyl-2-propenyl, 2-butenyl, 3-butenyl and the like;

$C_3$–$C_6$ alkynyl includes propargyl, 1-methyl-2-propynyl, 1,1-dimethyl-2-propynyl, 2-butynyl, 3-butynyl and the like;

benzyl which may be substituted with one or more of halogen, $C_1$–$C_6$ alkyl and $C_1$–$C_6$ alkoxy includes benzyl, 4-chlorobenzyl, 4-methylbenzyl and the like; and phenyl which may be substituted with one or more of halogen, $C_1$–$C_6$ alkyl and $C_1$–$C_6$ alkoxy includes phenyl, 4-chlorophenyl, p-tolyl, o-tolyl and the like.

Preferably, $A^1$ is methyl or amino, $A^2$ is $C_1$–$C_3$ alkyl substituted with fluorine, more preferably trifluoromethyl, X is fluorine, Y is chlorine, $R^2$ is hydrogen, $R^3$ is hydrogen, $R^4$ is hydrogen, $R^5$ is hydrogen and $R^1$ is —$OR^{21}$ (for $R^{21}$, hydrogen, $C_1$–$C_6$ alkyl, $C_3$–$C_6$ alkenyl or $C_3$–$C_6$ alkynyl are preferred.) or —$SR^{26}$ (for $R^{26}$, $C_1$–$C_6$ alkyl, $C_3$–$C_6$ alkenyl or $C_3$–$C_6$ alkynyl are preferred.) from the viewpoint of herbicidal activity.

Processes for producing the present compound will now be explained below. The present compound can be produced, for example, by processes described in [Process 1] to [Process 4] shown below. [Process 1]

A process for producing the present compound from a compound [I] by a production route shown in the following scheme:

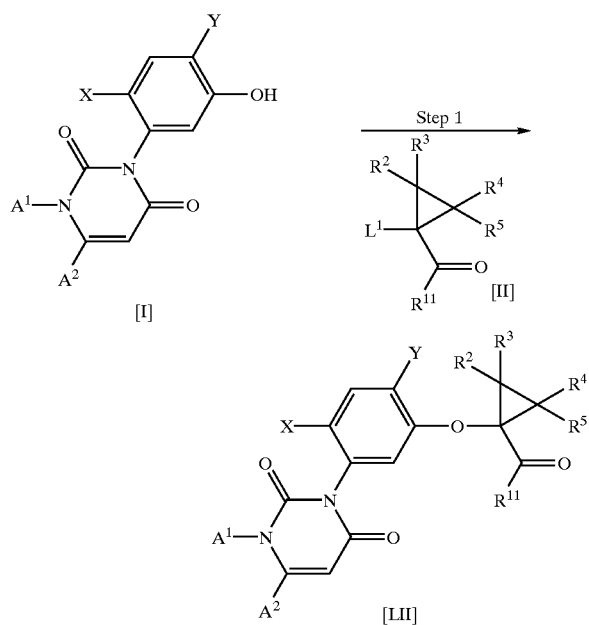

wherein $A^1$, $A^2$, X, Y, $R^2$, $R^3$, $R^4$ and $R^5$ are the same as defined above, $R^{11}$ represents a group of $R^1$ other than —OH and —SH and $L^1$ represents a leaving group including chlorine, bromine, iodine, methanesulfonyloxy, p-toluenesulfonyloxy and the like.

(Step 1)

The process is carried out by reacting compound [I] with compound [II] in a solvent or without solvent in the presence of a base.

Reaction temperature: −10 to 150° C.

Reaction period: a moment to 24 hours

Base material: organic base such as pyridine, triethylamine and the like and inorganic base such as sodium hydroxide, sodium hydride and the like Amount of base: While the theoretical amount is 1 mole on the basis of 1 mole of the compound [II], the amount thereof can optionally be varied within a range of 1 mole to an excess on the basis of 1 mole of the compound [II] according to the condition of the reaction.

Amount of compound [II] used in the reaction: While the theoretical amount is 1 mole on the basis of 1 mole of the compound [I], the amount thereof can optionally be varied within a range of 1 mole to an excess on the basis of 1 mole of the compound [I] according to the condition of the reaction.

Solvent material: acid amides including N,N-dimethylforamide (hereinafter, referred to as DMF) and the like and hydrocarbons including toluene and the like After the reaction is completed, the desired compound can be obtained by adding water to the reaction mixture and collecting the produced crystals, or adding water to the reaction mixture and applying the conventional post-treatment such as the extraction with an organic solvent and concentration or the like. The resulting compound can be purified by a treatment such as chromatography, recrystallization and the like.

[Process 2]

A process for producing the present compound from the compound [I] by a production route shown in the following scheme:

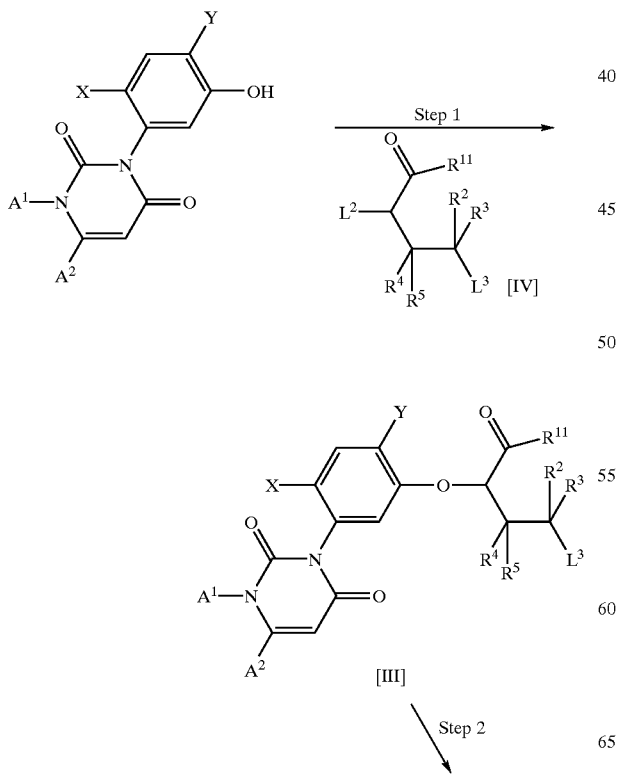

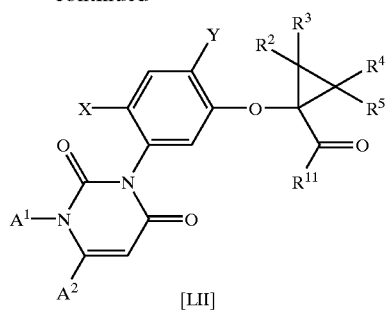

wherein $A^1$, $A^2$, X, Y, $R^{11}$, $R^2$, $R^3$, $R^4$ and $R^5$ are the same as defined above, $L^2$ represents a leaving group including chlorine, bromine, iodine, methanesulfonyloxy, p-toluenesulfonyloxy and the like and $L^3$ represents a leaving group including chlorine, bromine, iodine, methanesulfonyloxy, p-toluenesulfonyloxy and the like.

(Step 1)

The reaction is carried out by reacting compound [I] with compound [IV] in a solvent or without solvent in the presence of a base.

Reaction temperature: −10 to 150° C.

Reaction period: a moment to 24 hours

Base material: organic base such as pyridine, triethylamine and the like and inorganic base such as sodium hydroxide, sodium hydride, potassium carbonate and the like Amount of base: While the theoretical amount is 1 mole on the basis of 1 mole of the compound [IV], the amount thereof can optionally be varied within a range of 1 mole to an excess on the basis of 1 mole of the compound [IV] according to the condition of the reaction.

Amount of compound [IV] used in the reaction: While the theoretical amount is 1 mole on the basis of 1 mole of the compound [I], the amount thereof can optionally be varied within a range of 1 mole to an excess on the basis of 1 mole of the compound [I] according to the condition of the reaction.

Solvent material: acid amides including DMF and the like, hydrocarbons including toluene and the like and ethers including tetrahydrofuran (hereinafter, referred to as THF) and the like After the reaction is completed, the desired compound can be obtained by adding water to the reaction mixture and collecting the produced crystals, or adding water to the reaction mixture and applying the conventional post-treatment such as the extraction with an organic solvent and concentration or the like. The resulting compound can be purified by a treatment such as chromatography, recrystallization and the like.

(Step 2)
The reaction is carried out by reacting the compound [III] in a solvent in the presence of a base.
Reaction temperature: −10 to 150° C.

Reaction period: a moment to 24 hours

Base material: sodium hydride, potassium t-butoxide and the like

Amount of base: While the theoretical amount is 1 mole on the basis of 1 mole of the compound [III], the amount thereof can optionally be varied within a range of 1 mole to an excess on the basis of 1 mole of the compound [III] according to the condition of the reaction.

Solvent material: acid amides including DMF and the like, hydrocarbons including toluene and the like, ethers including THF and the like and secondary or tertiary alcohols including t-butanol and the like After the reaction is completed, the desired compound can be obtained by adding water to the reaction mixture and collecting the produced crystals, or adding water to the reaction mixture and applying the conventional post-treatment such as the extraction with an organic solvent and concentration or the like. The resulting compound can be purified by a treatment such as chromatography, recrystallization and the like.

In addition, the process can be performed by continuously carrying out the step 1 and the step 2 without isolating the compound [III].

[Process 3]
A process for producing the present compound from a compound [XXI] by a production route shown in the following scheme:

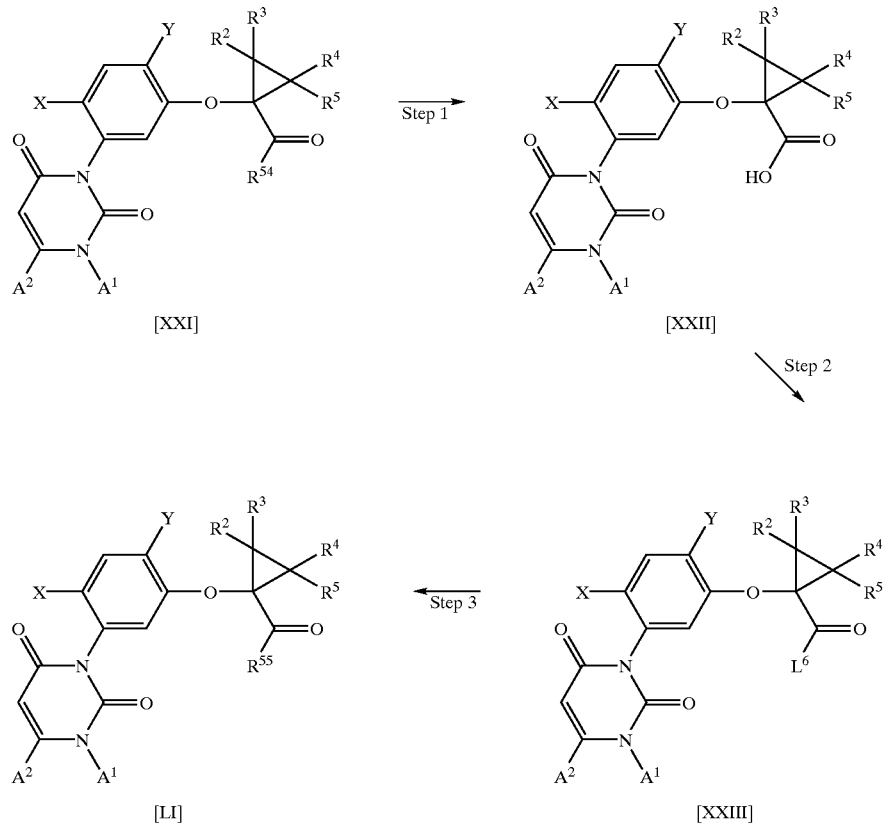

wherein $A^1, A^2, X, Y, R^1, R^2, R^3, R^4$ and $R^5$ are the same as defined above, $L^6$ represents chlorine or bromine, $R^{54}$ represents methoxy, ethoxy, t-butoxy, allyloxy or benzyloxy and $R^{55}$ represents a group of $R^1$ other than —OH.

(Step 1)
The reaction is carried out by hydrolyzing the ester moiety of the compound [XXI].

Specifically, the compound [XXII] can be produced, for example, by heating the compound [XXI] in concentrated hydrochloric acid or, when $R^{54}$ is benzyloxy, by treating the compound [XXI] in a hydrogen atmosphere in the presence of a Pd/c catalyst.

(Step 2)
The reaction is carried out by reacting the compound [XXII] with thionyl chloride or thionyl bromide.

(Step 3)
The reaction is carried out by reacting the compound [XXIII] with a compound of the formula

H—$R^{55}$ in the presence of a base such as pyridine, triethylamine or the like.

[Process 4]
A process for producing the present compound from a compound [VII] by a production route shown in the following scheme:

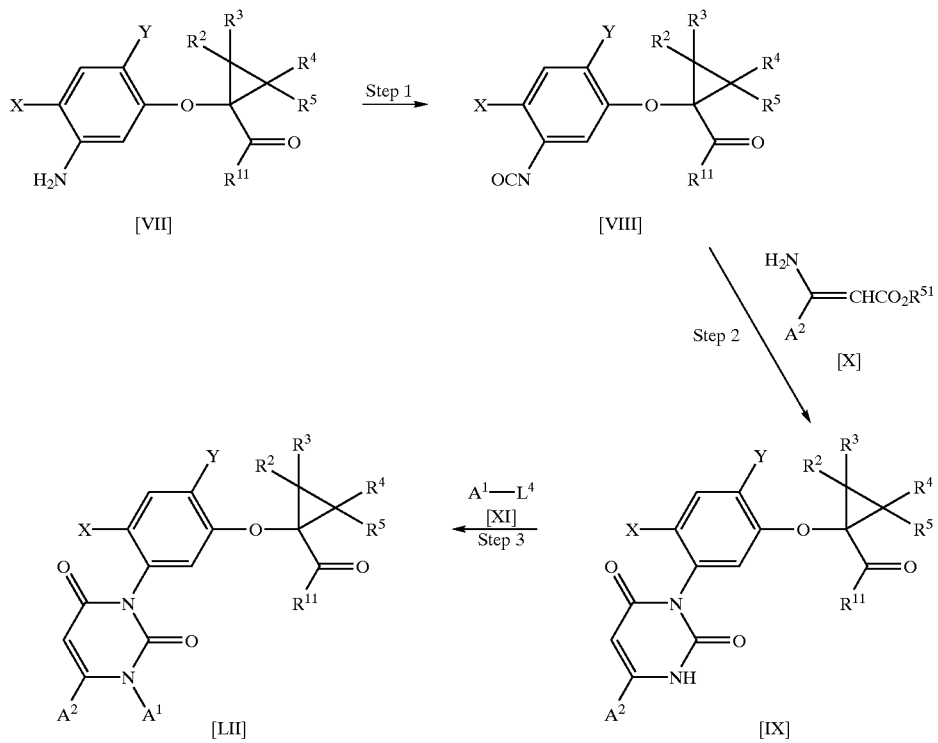

wherein $A^1$, $A^2$, X, Y, $R^{11}$, $R^2$, $R^3$, $R^4$ and $R^5$ are the same as defined above, $L^4$ represents a leaving group including chlorine, bromine, iodine, methanesulfonyloxy, p-toluenesulfonyloxy, 2,4-dinitrophenoxy and the like and $R^{51}$ represents $C_1$–$C_5$ alkyl (methyl, ethyl, isopropyl, t-butyl and the like) or benzyl.

(Step 1)

The reaction is carried out by reacting the compound [VII] with phosgene.

(Step 2)

The reaction is carried out by reacting the isocyanate compound [VIII] with the compound [X] in the presence of a base.

The compound [IX] can also be produced according to a process described in [Process 5] below.

(Step 3)

The reaction is carried out by reacting the compound [IX] with a compound [XI] in the presence of a base.

[Process 5]

A process for producing the compound [IX] from a compound [VII] by a production route shown in the following scheme:

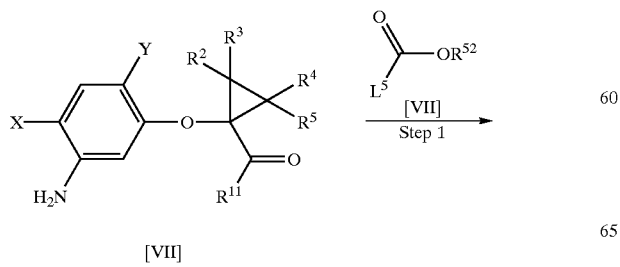

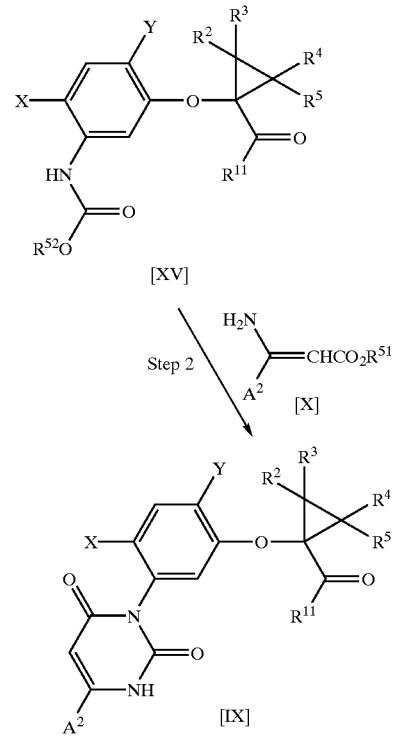

wherein $A^2$, X, Y, $R^{11}$, $R^{51}$, $R^2$, $R^3$, $R^4$ and $R^5$ are the same as defined above, $L^5$ represents chlorine, bromine or $C_1$–$C_5$ alkoxy (methoxy, ethoxy, isopropoxy and the like) and $R^{52}$ represents $C_1$–$C_5$ alkyl (methyl, ethyl, isopropyl, t-butyl and the like) or benzyl.

(Step 1)

The reaction is carried out by reacting the compound [VII] with the compound [XIV] in a solvent or without solvent in the presence of a base.

Reaction temperature: −15 to 150° C.

Reaction period: a moment to 24 hours

Base material: tertiary amine such as pyridine, triethylamine and the like

Amount of base: While the theoretical amount is 1 mole on the basis of 1 mole of the compound [VII], the amount thereof can optionally be varied within a range of 1 mole to an excess on the basis of 1 mole of the compound [VII] according to the condition of the reaction.

Amount of compound [XIV] used in the reaction: While the theoretical amount is 1 mole on the basis of 1 mole of the compound [VII], the amount thereof can optionally be varied within a range of 1 mole to an excess on the basis of 1 mole of the compound [VII] according to the condition of the reaction.

Solvent material: hydrocarbons including toluene, xylene and the like, acid amides including DMF and the like and ethers including THF, dioxane and the like After the reaction is completed, the desired compound can be obtained by adding water to the reaction mixture and collecting the produced crystals, or adding water to the reaction mixture and applying the conventional post-treatment such as the extraction with an organic solvent and concentration or the like. The resulting compound can be purified by a treatment such as chromatography, recrystallization and the like.

(Step 2)

The reaction is carried out by reacting the compound [XV] with the compound [X] in a solvent or without solvent in the presence of a base.

Reaction temperature: −15 to 150° C.

Reaction period: a moment to 24 hours

Base material: inorganic base including sodium hydride, sodium hydroxide, potassium t-butoxide and the like Amount of base: While the theoretical amount is 1 mole on the basis of 1 mole of the compound [XV], the amount thereof can optionally be varied within a range of 1 mole to an excess on the basis of 1 mole of the compound [XV] according to the condition of the reaction.

Amount of compound [X] used in the reaction: While the theoretical amount is 1 mole on the basis of 1 mole of the compound [XV], the amount thereof can optionally be varied within a range of 1 mole to an excess on the basis of 1 mole of the compound [XV] according to the condition of the reaction.

Solvent material: hydrocarbons including toluene, xylene and the like, acid amides including DMF and the like and ethers including THF, dioxane and the like After the reaction is completed, the desired compound can be obtained by adding water to the reaction mixture and collecting the produced crystals, or adding water to the reaction mixture and applying the conventional post-treatment such as the extraction with an organic solvent and concentration or the like. The resulting compound can be purified by a treatment such as chromatography, recrystallization and the like.

The compound [VII] can be produced according to processes described in [Process 6] and [Process 7] below.

[Process 6]

A process for producing the compound [VII] from a compound [XVI] by a production route shown in the following scheme:

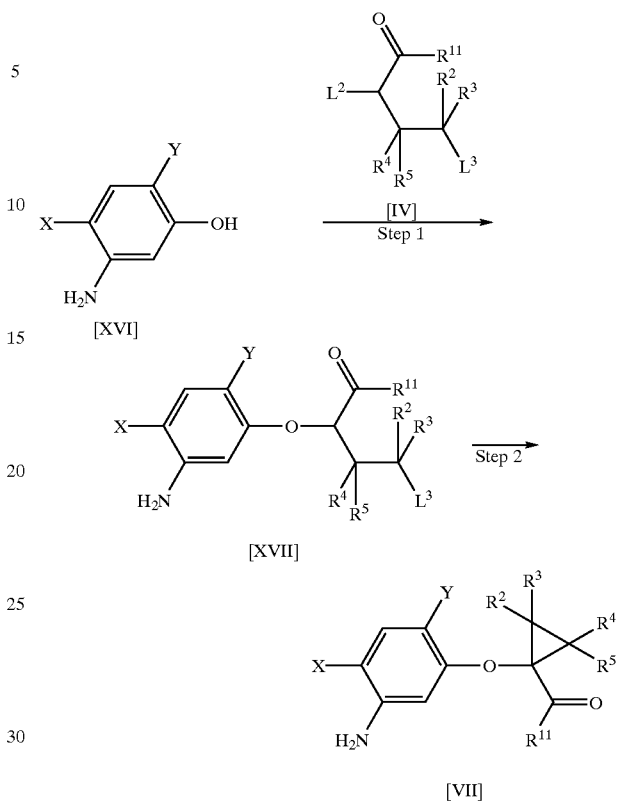

wherein X, Y, $R^{11}$, $R^2$, $R^3$, $R^4$, $R^5$, $L^2$ and $L^3$ are the same as defined above.

The process can be carried out according to the process described in Process 2 by using the compound [XVI] in place of the compound [I].

[Process 7]

A process for producing the compound [VII] from a compound [XVIII] by a production route shown in the following scheme:

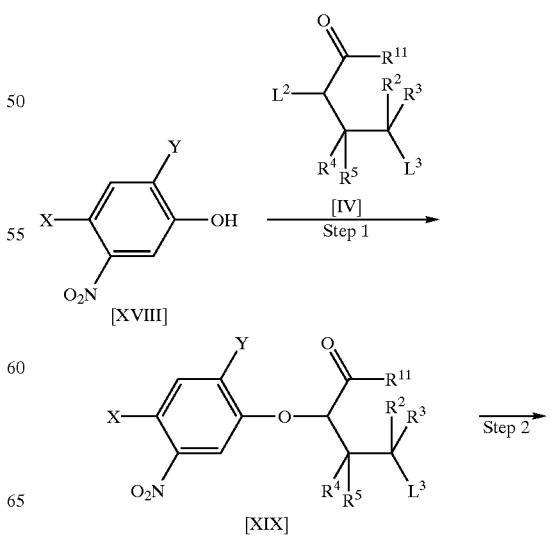

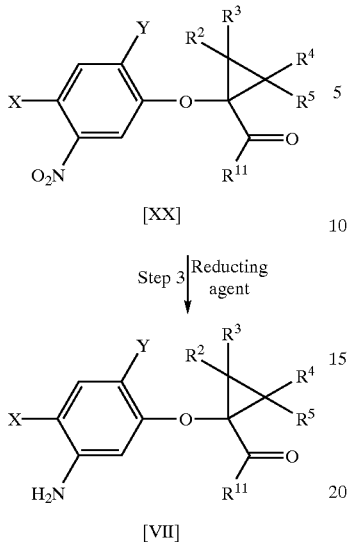

[XX]

Step 3 ↓ Reducting agent

[VII]

wherein X, Y, $R^{11}$, $R^2$, $R^3$, $R^4$, $R^5$, $L^2$ and $L^3$ are the same as defined above.

(Step 1) and (Step 2)

The reactions can be carried out according to the process described in Process 2 by using the compound [XVIII] in place of the compound [I]

(Step 3)

The reaction can be carried out by reducing the compound [XX] with a reducing agent such as iron powder.

The compound [I] can be produced according to processes described in U.S. Pat. No. 4,859,229, JP 11-508543A, JP 11-500714A, JP 11-510145A or WO 98/41093.

The compound [XVI] and the compound [XVIII] can be produced according to a process described EP 61741 A.

The present compounds have excellent herbicidal activity and some of them can exhibit excellent selectivity between crops and weeds. In other words, the present compounds have herbicidal activity against various weeds which may cause some trouble in the foliar treatment and soil treatment on upland fields, such as listed below.

Onagraceous weeds:
large-flowered eveningprimrose (*Oenothera erythrosepala*), Common eveningprimrose (*Oenothera biennis*), cutleaf eveningprimrose (*Oenothera laciniata*), Ranunculaceous weeds:
roughseeded buttercup (*Ranunculus muricatus*), hairy buttercup (*Ranunculus sardous*)

Polygonaceous weeds:
wild buckwheat (*Polygonum convolvulus*), pale smartweed (*Polygonum lapathifolium*), pennsylvania smartweed (*Polygonum pensylvanicum*) ladysthumb (*Polygonum persicaria*), curly dock (*Rumex crispus*), broadleaf dock (*Rumex obtusifolius*), Japanese knotweed (*Polygonum cuspidatum*), Prostrate knotweed (*Polygonum aviculare*), red sorrel (*Rumex acetosella*)

Portulacaceous weeds:
common purslane (*Portulaca oleracea*)

Caryophyllaceous weeds:
common chickweed (*stellaria media*), sticky chickweed (*Cerastium glomeratum*)

Chenopodiaceous weeds:
common lambsquarters (*Chenopodium album*), kochia (*Kochia scoparia*)

Amaranthaceous weeds:
redroot pigweed (*Amaranthus retroflexus*), smooth pigweed (*Amaranthus hybridus*), palmer amaranth (*Amaranthus palmeri*), tall waterhemp (*Amaranthus tuberculatus*), common waterhemp (*Amaranthus rudis*)

Cruciferous (brassicaceous) weeds:
wild radish (*Raphanus raphanistrum*), wild mustard (*Sinapis arvensis*), shepherdpurse (*Capsella bursa-pastoris*), virginia pepperweed (*Lepidium virginicum*)

Leguminous (fabaceous) weeds:
hemp sesbania (*Sesbania exaltata*), sicklepod (*Cassia obtusifolia*), Florida beggarweed (*Desmodium tortuosum*), white clover (*Trifolium repens*), common vetch (*Vicia sativa*), black medik (*Medicago lupulina*)

Papaveraceous weeds
Common poppy (*Papaver rhoeas*)

Malvaceous weeds:
velvetleaf (*Abutilon theophrasti*), pricklysida (*Sida spinosa*), venice mallow (*Hibiscus trionum*)

Violaceous weeds:
field pansy (*Viola arvensis*), wild pansy (*Viola tricolor*)

Rubiaceous weeds:
catchweed bedstraw (cleavers) (*Galium aparine*)

Convolvulaceous weeds:
ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*), hedge bindweed (*Calystegia sepium*)

Labiate weeds:
red deadnettle (*Lamium purpureum*), henbit (*Lamium amplexicaule*)

Solanaceous weeds:
jimsonweed (*Datura stramonium*), black nightshade (*Solanum nigrum*), Horsenettle (*Solanum carolinense*)

Scrophulariaceous weeds:
birdseye speedwell (*Veronica persica*) corn speedwell (*Veronica arvensis*), ivyleaf speedwell (*Veronica hederaefolia*)

Composite weeds:
common cocklebur (*Xanthium pensylvanicum*), common sunflower (*Helianthus annuus*), wild camomille (*Matricaria chamomilla*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*), late goldenrod (*Solidago gigantea*), common dandelion (*Taraxacum officinale*), Common groundsel (*Senecio vulgaris*), Hairy galinsoga (*Galinsoga ciliata*)

Boraginaceous weeds:
forget-me-not (*Myosotis scorpioides*), field forget-me-not (*Myosotis arvensis*)

Asclepiadaceous weeds:
common milkweed (*Asclepias syriaca*)

Euphorbiaceous weeds:
sun spurge (*Euphorbia helioscopia*), spotted spurge (*Euphorbia maculata*)

Geraniaceous weeds:
Carolina geranium (*Geranium carolinianum*)

Oxalidaceous weeds:
  pink woodsorrel (*Oxalis corymbosa*)
Cucurbitaceous weeds:
  burcucumber (*Sicyos angulatus*)
Graminaceous weeds:
  barnyardgrass (*Echinochloa crus-galli*), green foxtail (*Setaria viridis*), giant foxtail (*Setaria faberi*), large crabgrass (*Digitaria sanguinalis*), Southern Crabgrass (*Digitaria ciliaris*), goosegrass (*Eleusine indica*), annual bluegrass (*Poa annua*), blackgrass (*Alopecurus myosuroides*), wild oat (*Avena fatua*), Silky bentgrass (*Apera spica-venti*), johnsongrass (*Sorghum halepense*), quackgrass (*Agropyron repens*), downybrome (*Bromus tectorum*), bermudagrass (*Cynodon dactylon*), fall panicum (*Panicum dichotomiflorum*), Texas panicum (*Panicum texanum*), shattercane (*Sorghum vulgare*), woolly cupgrass(*Eriochloa villosa*), water foxtail (*Alopecurus geniculatus*)
Commelinaceous weeds:
  common dayflower (*Commelina communis*), tropical spiderwort (*Commelina benghalensis*)
Equisetaceous weeds:
  field horsetail (*Equisetum arvense*)
Cyperaceous weeds:
  rice flatsedge (*Cyperus iria*), purple nutsedge (*Cyperus rotundus*), yellow nutsedge (*Cyperus esculentus*)

Furthermore, some of the present compounds exhibit no significant phytotoxicity on the main crops including corn (*Zea mays*), wheat (*Triticum aestivum*), barley (*Hordeum vulgare*), rye (*Secale cereale*), oat (*Avena sativa*), rice (*Oryza sativa*), sorghum (*Sorghum bicolor*), soybean (*Glycine max*), cotton (Gossypium spp.), sugar beet (*Beta vulgaris*), peanut (*Arachis hypogaea*), sunflower (*Helianthus annuus*), and canola (*Brassica napus*); and horticultural crops such as flowers, ornamental plants, and vegetable crops.

The present compounds can also attain effective control of various weeds which can cause trouble in the no-tillage cultivation of soybean (*Glycine max*), corn (*Zea mays*), wheat (*Triticum aestivum*), and other crops. Furthermore, some of the present compounds exhibit no significant phytotoxicity on the crops.

The present compounds also have herbicidal activity against various weeds which may cause some trouble in flooding treatment of paddy fields, such as listed below.
Graminaceous weeds:
  barnyardgrass (*Echinochloa oryzicola*)
Scrophulariaceous weeds:
  common false pimpernel (*Lindernia procumbens*), low false pimpernel (*Lindernia dubia* var. *major*), moist bank pimpernel (*Lindernia dubia* var.*dubia*), yellowseed false pimpernel (*Lindernia anagallidea*), Lindelnia (*Lindernia micrantha*), suzumenotougarashi (*Lindernia antipoda*)
Lythraceous weeds:
  Indiantoothcup (*Rotala indica*), red stem (*Ammannia multiflora*), valley redstem (*Ammannia coccinea*)
Elatinaceous weeds:
  waterwort (*Elatine triandra*)
Cyperaceous weeds:
  smallflower umbrella sedge (*Cyperus difformis*), hardstem bulrush (*Scirpus juncoides* subsp. *hotarui*), inuhotarui (*Scirpus juncoides* subsp. *juncoides*), needle spikerush (*Eleocharis acicularis*), water nutgrass (*Cyperus serotinus*), water chestnut (*Eleocharis kuroguwai*)
Pontederiaceous weeds:
  monochoria (*Monochoria vaginalis*)
Alismataceous weeds:
  arrowhead (*Sagittaria pygmaea*), arrowhead (*Sagittaria trifolia*), waterplantain (*Alisma canaliculatum*)
Potamogetonaceous weeds:
  roundleaf pondweed (*Potamogeton distinctus*)
Umbelliferous weeds:
  watercelery sp. (*Oenanthe javanica*)

Furthermore, some of the present compounds exhibit no significant phytotoxicity on transplanted paddy rice.

The present compounds can also be used to control a wide variety of weeds which are growing or will grow in other non-cultivated lands in which weed controlling is necessitated such as a levee, riverbed, roadside, railroad, green field area of a park, ground, parking area, airport, industrial place (ex. factory, storage equipment), fallow land, vacant lot, orchards, grasslands, lawns, forests, and the like. The present compounds also have herbicidal activity against various aquatic weeds, such as water hyacinth (*Eichhornia crassipes*), which are growing or will grow at the waterside such as rivers, canals, waterways or reservoirs.

Furthermore, where crops with tolerance imparted by introducing a herbicide tolerance gene as described in WO 95/34659 are cultivated, the present compounds can be used at larger rates than those used when ordinary crops without tolerance are cultivated, which makes it possible to control other unfavorable weeds more effectively.

When the present compounds are used as the active ingredients of herbicides, they may be suitably mixed with solid or liquid carriers or diluents, surfactants, and other auxiliary agents to give emulsifiable concentrates, wettable powders, flowables, granules, concentratedemulsions, water-dispersible granules, or other formulations.

These formulations may contain any of the present compounds as an active ingredient at an amount of about 0.001 to about 80% by weight, preferably about 0.005 to about 70% by weight, based on the total weight of the formulation.

Solid carriers for use in the present invention include, fine powders of mineral matters such as kaolin clay, attapulgite clay, bentonite, acid clay, pyrophyllite, talc, diatomaceous earth, and calcite; fine powders of organic substances such as walnut shell powder; fine powders of water-soluble organic substances such as urea; fine powders of inorganic salts such as ammonium sulfate; and fine powders of synthetic hydrated silicon oxide. Liquid carriers for use in the present invention include, aromatic hydrocarbons such as methylnaphthalene, phenylxylylethane, and alkylbenzene (e.g., xylene); alcohols such as isopropanol, ethylene glycol, and 2-ethoxyethanol; esters such as phthalic acid dialkyl esters; ketones such as acetone, cyclohexanone, and isophorone; mineral oils such as machine oil; vegetable oils such as soybean oil and cottonseed oil; dimethyl sulfoxide, N,N-dimethylformamide, acetonitrile, N-methylpyrrolidone, water and the like. Other carriers suitable for use in the present invention will be apparent to one skilled in the art.

The surfactant used for emulsification, dispersing, or spreading may include surfactants of the anionic type, such as alkylsulfates, alkylsulfonates, alkylarylsulfonates, dialkylsulfosuccinates, and phosphates of polyoxyethylene alkyl aryl ethers; and surfactants of the nonionic type, such as polyoxyethylene alkyl ethers, polyoxyethylene alkyl aryl ethers, polyoxyethylene polyoxypropylene block copolymers, sorbitan fatty acid esters, and polyoxyethylene sorbitan fatty acid esters. Other surfactants suitable for use in the present invention will be apparent to one skilled in the art.

Other auxiliary agents that may be utilized in the present invention include lignin sulfonates, alginates, polyvinyl alcohol, gum arabic, CMC (carboxymethylcellulose), and PAP (isopropyl acid phosphate). Other auxiliary agents suitable for use in the present invention will be apparent to one skilled in the art.

The present compounds are usually formulated and then used for soil, foliar, or flooding treatment at pre- or post-emergence of weeds. The soil treatment may include soil surface treatment and soil incorporation. The foliar treatment may include application over the plants and directed application in which a chemical is applied only to weeds so as to keep it off the crop plants.

The present compounds may often exhibit the enhancement of herbicidal activity when used in admixture with other herbicides. They can also be used in admixture with insecticides, acaricides, nematocides, fungicides, bactericides, plant growth regulators, fertilizers, and soil conditioners.

The present compounds may, for example, be used in admixture with the following herbicides: atrazine, cyanazine, dimethametryn, metribuzin, prometryn, simazine, simetryn, chlorotoluron, diuron, fluometuron, isoproturon, linuron, methabenzthiazuron, propanil, bentazone, bromoxynil, ioxynil, pyridate, butamifos, dithiopyr, ethalfluralin, pendimethalin, thiazopyr, trifluralin, acetochlor, alachlor, butachlor, diethatyl-ethyl, dimethenamid, fluthiamide, mefenacet, metolachlor, pretilachlor, propachlor, cinmethylin, acifluorfen, acifluorfen-sodium, benzfendizone, bifenox, butafenacil, chlomethoxynil, fomesafen, lactofen, oxadiazon, oxadiargyl, oxyfluorfen, carfentrazone-ethyl, fluazolate, flumiclorac-pentyl, flumioxazine, fluthiacet-methyl, isopropazol, sulfentrazone, thidiazimin, azafenidin, pyraflufen-ethyl, cinidon-ethyl, difenzoquat, diquat, paraquat, 2,4-D, 2,4-DB, clopyralid, dicamba, fluroxypyr, MCPA, MCPB, mecoprop, quinclorac, triclopyr, azimsulfuron, bensulfuron-methyl, chlorimuron-ethyl, chlorsulfuron, cloransulam-methyl, cyclosulfamuron, diclosulam, ethoxysulfuron, flazasulfuron, flucarbazone, flumetsulam, flupyrsulfuron, halosulfuron-methyl, imazosulfuron, indosulfuron, metosulam, metsulfuron-methyl, nicosulfuron, oxasulfuron, primisulfuron-methyl, procarbazone-sodium, prosulfuron, pyrazosulfuron-ethyl, rimsulfuron, sulfometuron-methyl, sulfosulfuron, triasulfuron, tribenuron-methyl, tritosulfuron, thifensulfuron-methyl, triflusulfuron-methyl, pyribenzoxim, bispyribac-sodium, pyriminobac-methyl, pyrithiobac-sodium, imazameth, imazamethabenz-methyl, imazamox, imazapic, imazapyr, imazaquin, imazethapyr, tepraloxydim, alloxydim-sodium, clethodim, clodinafop-propargyl, cyhalofop-butyl, dichlofop-methyl, fenoxaprop-ethyl, fenoxaprop-p-ethyl, fluazifop-buthyl, fluazifop-p-butyl, haloxyfop-methyl, quizalofop-p-ethyl, sethoxydim, tralkoxydim, diflufenican, flurtamone, norflurazon, benzofenap, isoxaflutole, pyrazolate, pyrazoxyfen, sulcotrione, clomazone, mesotrione, isoxachlortole, bialaphos, glufosinate-ammonium, glyphosate, sulfosate, dichlobenil, isoxaben, benthiocarb, butylate, dimepiperate, EPTC, esprocarb, molinate, pyributicarb, triallate, iflufenzopyr, bromobutide, DSMA, MSMA, cafenstrol, daimron, epoprodan, flupoxam, metobenzuron, pentoxazone, piperophos, triaziflam, beflubutamid, benzobicyclon, clomeprop, fentrazamide, flufenacet, florasulam, indanofan, isoxadifen, mesotrione, naploanilide, oxaziclomefone, pethoxyamid, phnothiol, and pyridafol.

The above compounds are described in the catalog of Farm Chemicals Handbook, 1995 (Meister Publishing Company); AG CHEM NEW COMPOUND REVIEW, VOL. 13, 1995, VOL. 15, 1997, or VOL. 16, 1998 or, AGROW No. 296 p22, No. 297 p21, No. 308 p22, or No. 324 p26-27, or Josouzai Kenkyu Souran (Hakuyu-sha).

When the present compounds are used as the active ingredients of herbicides, the application amount, although it may vary with the weather conditions, formulation types, application times, application methods, soil conditions, crops to be protected, and weeds to be controlled, etc. is preferably in the range of about 0.01 to about 20,000 g, more preferably about 1 to about 12,000 g, per hectare. In the case of emulsifiable concentrates, wettable powders, flowables, concentrated emulsions, water-dispersible granules, or the like, they are usually applied after being diluted in their prescribed amounts with water (if necessary, containing an adjuvant such as a spreading agent) at a ratio of about 10 to about 1000 liters per hectare. In the case of granules or some types of flowables, they are usually applied as such without any dilution.

The adjuvant which can be used, if necessary, may include, in addition to the surfactants as described above, polyoxyethylene resin acids (esters), lignin sulfonates, abietates, dinaphthylmethanedisulfonates, crop oil concentrates, and vegetable oils such as soybean oil, corn oil, cottonseed oil, and sunflower oil. Other adjuvants suitable for use in the present invention will be apparent to one skilled in the art.

The present compounds can also be used as the active ingredients of harvesting aids such as defoliants and desiccants for cotton (Gossipyum spp.), and desiccants for potato (*Solanum tuberosum*). In these cases, the present compounds are usually formulated in the same manner as when they are used as the active ingredients of herbicides, and may be used alone or in admixture with other harvesting aids for foliar treatment before the harvesting of crops.

EXAMPLES

The invention will now be described in more detail with reference to Production Examples, Formulation Examples and Test Examples, which should not be construed as a limitation upon the scope of the invention. Compound Numbers given to specific compounds in the examples are the same as those shown in Table 1 described below.

Production Example 1
[Production of Compound 1–2]

Into 20 ml of DMF were dissolved 2.0 g of 2-chloro-4-fluoro-5-{3-methyl-2,6-dioxo-4-(trifluoromethyl)-1,2,3,6-tetrahydropyrimidin-1-yl}phenol and 2.0 g of methyl 2,4-dibromobutanoate (purity: 70%; produced in Reference Production Example 1 described below). To the solution was added 1.0 g of potassium carbonate and the mixture was stirred at room temperature for 2 hours. The reaction mixture was poured into aqueous diluted hydrochloric acid and the mixture was extracted with ethyl acetate. The organic layer was washed with water and saturated aqueous sodium chloride solution in turn and dried over anhydrous magnesium sulfate. Then the resultant was concentrated under reduced pressure and the residue was subjected to silica gel chromatography (eluent: hexane/ethyl acetate=5/1) to give 2.3 g of methyl 2-[2-chloro-4-fluoro-5-{3-methyl-2,6-dioxo-4-(trifluoromethyl)-1,2,3,6-tetrahydropyrimidin-1-yl}phenxy]-4-bromobutanoate.

$^1$H-NMR (300 MHz, CDCl$_3$, TMS δ (ppm)): 2.42–2.68 (2H, m), 3.54–3.56 (3H, m), 3.59–3.69 (2H, m), 3.76 (3H, s), 4.78–4.84 (1H, m), 6.35 (1H, s), 6.79–6.85 (1H, m), 7.32 (1H, d, J=8.9 Hz)

Into 10 ml of THF was dissolved 0.44 g of the obtained methyl 2-[2-chloro-4-fluoro-5-{3-methyl-2,6-dioxo-4-(trifluoromethyl)-1,2,3,6-tetrahydropyrimidin-1-yl}phenoxy]-4-bromobutanoate and 0.10 g of potassium t-butoxide was added to the solution at −15° C. Cooling bath was removed and the solution was stirred until the solution became room temperature taking 2 hours. The reaction solution was poured into aqueous diluted hydrochloric acid and the mixture was extracted with ethyl acetate. The organic layer was dried over anhydrous magnesium sulfate, filtered and concentrated under reduced pressure. The residue was subjected to silica gel chromatography (eluent:hexane/ethyl acetate=4/1) to give 0.26 g of methyl 1-[2-chloro-4-fluoro-5-{3-methyl-2,6-dioxo-4-(trifluoro-methyl)-1,2,3,6-tetrahydropyrimidin-1-yl}phenoxy]cyclopropanecarboxylate (Compound 1-2).

$^1$H-NMR (300 MHz, CDCl$_3$, TMS δ (ppm)): 1.38–1.43 (2H, m), 1.61–1.66 (2H, m), 3.55–3.56 (3H, m), 3.73 (3H, s), 6.35 (1H, s), 6.84 (1H, d, J=6.4 Hz), 7.30 (1H, d, J=8.7 Hz)

Production Example 2
[Production of Compound 1-3]

To a solution containing 2-chloro-4-fluoro-5-nitrophenol (1 equivalent) and ethyl 2,4-dibromobutanoate (1 equivalent) in DMF is added potassium carbonate (1 equivalent) at room temperature and the mixture is stirred. After completion of the reaction, to the reaction mixture is added aqueous diluted hydrochloric acid and the mixture is extracted with ethyl acetate. After concentrating the organic layer, the residue is subjected to chromatography to give ethyl 2-(2-chloro-4-fluoro-5-nitrophenoxy)-4-bromobutanoate.

To a solution containing the obtained ethyl 2-(2-chloro-4-fluoro-5-nitrophenoxy)-4-bromobutanoate (1 equivalent) in THF is added potassium t-butoxide (1 equivalent) at −15° C. and the mixture is stirred. After warming the reaction solution up to room temperature, to the solution is added aqueous diluted hydrochloric acid and extracted with ethyl acetate. After concentrating the organic layer, the residue is subjected to chromatography to give ethyl 1-(2-chloro-4-fluoro-5-nitrophenoxy)cyclopropanecarboxylate.

The obtained ethyl 1-(2-chloro-4-fluoro-5-nitro-phenoxy)cyclopropanecarboxylate (1 equivalent) is added dropwise to a mixture of acetic acid/ water (1/1) containing iron powders (3 equivalents) at 6° C. After completion of addition, the mixture is allowed to cool to room temperature and extracted with ethyl acetate. After concentrating the organic layer, the residue is subjected to chromatography to give ethyl 1-(2-chloro-4-fluoro-5-aminophenoxy) cyclopropanecarboxylate.

The obtained ethyl 1-(2-chloro-4-fluoro-5-aminophenoxy)cyclopropanecarboxylate (1 equivalent) and dimethylaniline (1 equivalent) are added to THF and ethyl chloroformate (1 equivalent) is gradually added in drops thereto. After completion of addition, to the reaction solution is added aqueous diluted hydrochloric acid and the mixture is extracted with ethyl acetate. After concentrating the organic layer, the residue is subjected to chromatography to give ethyl 1-(2-chloro-4-fluoro-5-ethoxycarbonylaminophenoxy)cyclo-propanecarboxylate.

The obtained ethyl 1-(2-chloro-4-fluoro-5-ethoxycarbonylaminophenoxy)cyclopropanecarboxylate is added dropwise to a solution containing sodium hydride (1 equivalent) and CF$_3$C(NH$_2$)=CHCO$_2$Et (1 equivalent) in DMF and the solution is stirred under heating to 130° C. After cooling to room temperature, iodomethane (1 equivalent) is added thereto and the mixture is stirred. After completion of reaction, to the reaction solution is added aqueous diluted hydrochloric acid and the mixture is extracted with ethyl acetate. After concentrating the organic layer, the residue is subjected to chromatographytogive ethyl 1-[2-chloro-4-fluoro-5-{3-methyl-2,6-dioxo-4-(trifluoromethyl)-1,2,3,6-tetrahydropyrimidin-1-yl}phenoxy]cyclopropanecarboxylate (Compound 1-3).

Production Example 3
[Production of Compound 1-1]

2.0 g of methyl 1-[2-chloro-4-fluoro-5-{3-methyl-2,6-dioxo-4-(trifluoromethyl)-1,2,3,6-tetrahydropyrimidin-1-yl}phenoxy]cyclopropanecarboxylate was dissolved in a solution consisting of 10 ml of 1,4-dioxane and 10 ml of conc. hydrochloric acid, and the obtained solution was heated under reflux for 2 hours. The reaction mixture was poured into ice water and extracted with ethyl acetate. The organic layer was washed with water and saturated aqueous sodium chloride solution in turn, and dried over anhydrous magnesium sulfate. The resultant was concentrated under reduced pressure. The produced crystals was washed with a mixed solution of hexane and t-butyl methyl ether to give 1.2 g of 1-[2-chloro-4-fluoro-5-{3-methyl-2,6-dioxo-4-(trifluoro-methyl)-1,2,3,6-tetrahydropyrimidin-1-yl}phenoxy]cyclo-propanecarboxylic acid (Compound 1-1).

$^1$H-NMR (300MHZ, CDCl$_3$, TMSδ (ppm)): 1.40–1.48 (2H, m), 1.63–1.70 (2H, m), 3.55 (3H, s ), 6.36 (1H, s), 6.93 (1H, d, J=6.4 Hz), 7.29 (1H, d, J=8.7 Hz), 7.55 (1H, br)

Process for producing the raw material for preparation of compounds within the scope of the present invention will now be described as Reference Production Example.

Reference Production Example 1
[Production of methyl 2,4-dibromobutanoate]

To a mixed solution of 8.6 g of γ-butyrolactone and 4.7 ml of phosphorus tribromide was added dropwise 16.8 g of bromine at 100° C. After completion of addition, the mixture was stirred under heating at 120° C. for 1 hour until generation of gas from the system terminated. The solution was cooled to 10° C. and 100 ml of methanol was gradually added dropwise thereto. After adding 10 ml of concentrated hydrochloric acid, the solution was further stirred at room temperature for 2 hours. After concentrating the reaction solution under reduced pressure, to the residue was added water and the mixture was extracted with t-butyl methyl ether. The organic layer was washed with water, saturated aqueous sodium hydrogen carbonate solution and saturated aqueous sodium chloride solution in turn, dried over magnesium sulfate and concentrated. The residue was distilled under reduced pressure to give 12.5 g of methyl 2,4-dibromobutanoate in 70% purity and 2.0 g of methyl 2,4-dibromobutanoate in 100% purity.

$^1$H-NMR (250 MHz, CDCl$_3$, TMS δ (ppm)) 2.48–2.57 (2H, m), 3.55 (2H, t, J=6.1 Hz), 3.81 (3H, s), 4.50–4.56 (1H, m)

Reference Production Example 2

1.2 g of 1-[2-chloro-4-fluoro-5-{3-methyl-2,6-dioxo-4-(trifluoromethyl)-1,2,3,6-tetrahydropyrimidin-1-yl}phenoxy]cyclopropanecarboxylic acid was dissolved in 12 ml of thionyl chloride and the solution was heated under reflux for 2 hours. The reaction mixture was concentrated under reduced pressure to obtain 1-[2-chloro-4-fluoro-5-{3-methyl-2,6-dioxo-4-(trifluoromethyl)-1,2,3,6-tetrahydropyrimidin-1-yl}phenoxy]cyclopropanecarboxylic acid chloride.

Examples of compounds within the scope of the present invention are listed in Tables 1 and 2 together with Compound Numbers. It is to be appreciated, however, that the present invention is not limited to these examples.

TABLE 1

| Compound No. | X | Y | $A^1$ | $R^1$ |
|---|---|---|---|---|
| 1-1 | F | Cl | $CH_3$ | OH |
| 1-2 | F | Cl | $CH_3$ | $OCH_3$ |
| 1-3 | F | Cl | $CH_3$ | $OC_2H_5$ |
| 1-4 | F | Cl | $CH_3$ | $OCH(CH_3)_2$ |
| 1-5 | F | Cl | $CH_3$ | $OCH_2CH_2CH_3$ |
| 1-6 | F | Cl | $CH_3$ | $OCH_2CH(CH_3)_2$ |
| 1-7 | F | Cl | $CH_3$ | $OCH_2CH=CH_2$ |
| 1-8 | F | Cl | $CH_3$ | $CCH_2C\equiv CH$ |
| 1-9 | F | Cl | $CH_3$ | $OCH_2CO_2H$ |
| 1-10 | F | Cl | $CH_3$ | $OCH(CH_3)CO_2H$ |
| 1-11 | F | Cl | $CH_3$ | $OCH_2CO_2CH_3$ |
| 1-12 | F | Cl | $CH_3$ | $OCH_2CO_2C_2H_5$ |
| 1-13 | F | Cl | $CH_3$ | $OCH_2CO_2CH_2CH=CH_2$ |
| 1-14 | F | Cl | $CH_3$ | $OCH(CH_3)CO_2CH_3$ |
| 1-15 | F | Cl | $CH_3$ | $OCH(CH_3)CO_2CH_2CH=CH_2$ |
| 1-16 | F | Cl | $CH_3$ | $OC(CH_3)_2CO_2CH_3$ |
| 1-17 | F | Cl | $CH_3$ | $OCH_2CH_2OCH_3$ |
| 1-18 | F | Cl | $CH_3$ | $OCH_2C_6H_5$ |
| 1-19 | F | Cl | $CH_3$ | $SCH_3$ |
| 1-20 | F | Cl | $CH_3$ | $SC_2H_5$ |
| 1-21 | F | Cl | $CH_3$ | $SCH_2CO_2CH_3$ |
| 1-22 | F | Cl | $CH_3$ | $SCH(CH_3)CO_2CH_3$ |
| 1-23 | F | Cl | $CH_3$ | $NH_2$ |
| 1-24 | F | Cl | $CH_3$ | $NHCH_3$ |
| 1-25 | F | Cl | $CH_3$ | $N(CH_3)_2$ |
| 1-26 | F | Cl | $CH_3$ | $NHCH_2CO_2CH_3$ |
| 1-27 | F | Cl | $CH_3$ | $NHCH(CH_3)CO_2CH_3$ |
| 1-28 | F | Cl | $CH_3$ | $NHCH(CH_2CH(CH_3)_2)CO_2CH_3$ |
| 1-29 | F | Cl | $CH_3$ | $NHOCH_3$ |
| 1-30 | F | Cl | $CH_3$ | $NHOC_2H_5$ |
| 1-31 | F | Cl | $CH_3$ | $N(CH_3)OCH_3$ |
| 1-32 | F | Cl | $CH_3$ | $NHSO_2CH_3$ |
| 1-33 | F | Cl | $CH_3$ | $NHSO_2CH_2Cl$ |
| 1-34 | F | Cl | $CH_3$ | $ON(CH_3)_2$ |
| 1-35 | F | Cl | $CH_3$ | $ON(C_2H_5)_2$ |
| 1-36 | F | Cl | $CH_3$ | $ON=C(CH_3)_2$ |
| 1-37 | F | Cl | $CH_3$ | $ON=C(CH_3)(CH_2CH(CH_3)_2)$ |
| 1-38 | F | Cl | $CH_3$ | $NHN(CH_3)_2$ |
| 1-39 | F | Cl | $NH_2$ | OH |
| 1-40 | F | Cl | $NH_2$ | $OCH_3$ |
| 1-41 | F | Cl | $NH_2$ | $OC_2H_5$ |
| 1-42 | F | Cl | $NH_2$ | $OCH(CH_3)_2$ |
| 1-43 | F | Cl | $NH_2$ | $OCH_2CH_2CH_3$ |
| 1-44 | F | Cl | $NH_2$ | $OCH_2CH(CH_3)_2$ |
| 1-45 | F | Cl | $NH_2$ | $OCH_2CH=CH_2$ |
| 1-46 | F | Cl | $NH_2$ | $OCH_2C\equiv CH$ |
| 1-47 | F | Cl | $NH_2$ | $OCH_2CO_2H$ |
| 1-48 | F | Cl | $NH_2$ | $OCH(CH_3)CO_2H$ |
| 1-49 | F | Cl | $NH_2$ | $OCH_2CO_2CH_3$ |
| 1-50 | F | Cl | $NH_2$ | $OCH_2CO_2C_2H_5$ |
| 1-51 | F | Cl | $NH_2$ | $OCH_2CO_2CH_2CH=CH_2$ |
| 1-52 | F | Cl | $NH_2$ | $OCH(CH_3)CO_2CH_3$ |
| 1-53 | F | Cl | $NH_2$ | $OCH(CH_3)CO_2CH_2CH=CH_2$ |
| 1-54 | F | Cl | $NH_2$ | $OC(CH_3)_2CO_2CH_3$ |
| 1-55 | F | Cl | $NH_2$ | $OCH_2CH_2OCH_3$ |
| 1-56 | F | Cl | $NH_2$ | $OCH_2C_6H_5$ |
| 1-57 | H | Cl | $CH_3$ | $OCH_3$ |
| 1-58 | H | Cl | $NH_2$ | $OCH_3$ |
| 1-59 | H | Cl | $CH_3$ | $OC_2H_5$ |
| 1-60 | H | Cl | $NH_2$ | $OC_2H_5$ |
| 1-61 | Cl | Cl | $CH_3$ | $OCH_3$ |
| 1-62 | Cl | Cl | $NH_2$ | $OCH_3$ |
| 1-63 | Cl | Cl | $CH_3$ | $OC_2H_5$ |
| 1-64 | Cl | Cl | $NH_2$ | $OC_2H_5$ |
| 1-65 | F | F | $CH_3$ | $OCH_3$ |
| 1-66 | F | F | $NH_2$ | $OCH_3$ |
| 1-67 | F | F | $CH_3$ | $OC_2H_5$ |
| 1-68 | F | F | $NH_2$ | $OC_2H_5$ |
| 1-69 | F | Br | $CH_3$ | $OCH_3$ |
| 1-70 | F | Br | $NH_2$ | $OCH_3$ |
| 1-71 | F | Br | $CH_3$ | $OC_2H_5$ |
| 1-72 | F | Br | $NH_2$ | $OC_2H_5$ |

TABLE 2

| Compound No. | X | Y | $A^1$ | $R^1$ | $R^2$ | $R^3$ | $R^4$ | $R^5$ |
|---|---|---|---|---|---|---|---|---|
| 2-1 | F | Cl | $CH_3$ | OH | $CH_3$ | H | H | H |
| 2-2 | F | Cl | $CH_3$ | OH | $CH_3$ | H | $CH_3$ | H |
| 2-3 | F | Cl | $CH_3$ | OH | $CH_3$ | $CH_3$ | H | H |
| 2-4 | F | Cl | $CH_3$ | OH | $C_2H_5$ | H | H | H |
| 2-5 | F | Cl | $CH_3$ | $OCH_3$ | $CH_3$ | H | H | H |
| 2-6 | F | Cl | $CH_3$ | $OCH_3$ | $CH_3$ | H | $CH_3$ | H |
| 2-7 | F | Cl | $CH_3$ | $OCH_3$ | $CH_3$ | $CH_3$ | H | H |
| 2-8 | F | Cl | $CH_3$ | $OCH_3$ | $C_2H_5$ | H | H | H |
| 2-9 | F | Cl | $CH_3$ | $OC_2H_5$ | $CH_3$ | H | H | H |
| 2-10 | F | Cl | $CH_3$ | $OC_2H_5$ | $CH_3$ | H | $CH_3$ | H |
| 2-11 | F | Cl | $CH_3$ | $OC_2H_5$ | $CH_3$ | $CH_3$ | H | H |
| 2-12 | F | Cl | $CH_3$ | $OC_2H_5$ | $C_2H_5$ | H | H | H |
| 2-13 | H | Cl | $CH_3$ | OH | $CH_3$ | H | H | H |
| 2-14 | H | Cl | $CH_3$ | $OCH_3$ | $CH_3$ | H | H | H |
| 2-15 | H | Cl | $CH_3$ | $OC_2H_5$ | $CH_3$ | H | H | H |
| 2-16 | Cl | Cl | $CH_3$ | OH | $CH_3$ | H | H | H |
| 2-17 | Cl | Cl | $CH_3$ | $OCH_3$ | $CH_3$ | H | H | H |
| 2-18 | Cl | Cl | $CH_3$ | $OC_2H_5$ | $CH_3$ | H | H | H |
| 2-19 | F | F | $CH_3$ | OH | $CH_3$ | H | H | H |
| 2-20 | F | F | $CH_3$ | $OCH_3$ | $CH_3$ | H | H | H |
| 2-21 | F | F | $CH_3$ | $OC_2H_5$ | $CH_3$ | H | H | H |
| 2-22 | F | Cl | $NH_2$ | OH | $CH_3$ | H | H | H |
| 2-23 | F | Cl | $NH_2$ | $OCH_3$ | $CH_3$ | H | H | H |
| 2-24 | F | Cl | $NH_2$ | $OC_2H_5$ | $CH_3$ | H | H | H |

The physical properties (melting point, $^1$H-NMR (300 MHz, CDCl$_3$, TMS, δ (ppm))) of the exemplified compounds are shown below. (The compound Nos. 1-3, 1-7, 1-19 and 1-28 were produced by using the compound obtained in Reference Production Example 2.)

Compound No. 1–3:
1.18(3H,t,J=7.1 Hz), 1.37–1.42(2H,m), 1.58–1.64(2H,m), 3.55(3H,m), 4.19(2H,d,J=7.1 Hz), 6.35(1H,s), 6.86(1H,d,J=6.8Hz), 7.30(1H,d,J=9.0 Hz)

Compound No. 1-7:
1.39–1.45(2H,m), 1.61–1.67(2H,m), 3.55(3H,m), 4.62(2H,d,J=5.9 Hz), 5.16–5.26(2H,m), 5.75–5.89(1H,m), 6.35(1H,s), 6.88(1H,d,J=6.4 Hz), 7.30(1H,d,J=8.6 Hz)

Compound No. 1-19:
1.42–1.47(2H,m), 1.69–1.75(2H,m), 2.29(3H,s), 3.55(3H,s), 6.35(1H,s), 6.88(1H,d,J=6.4 Hz), 7.32(1H,d,J=8.8 Hz)

Compound No. 1-28:
0.77–0.89(6H,m), 0.98–1.12(1H,m), 1.23–1.40(3H,m), 1.51–1.61(1H,m), 1.62–1.72(1H,m), 1.80–1.91(1H,m), 3.54(3H,q,J=1.4 Hz), 3.68(3H,s), 4.52(1H,m), 6.33(1H,m), 6.83(1H,d,J=8.5 Hz), 6.98–7.03(1H,m), 7.32(1H,d,J=8.9 Hz)

Next, formulation examples of the compounds within the scope of the present invention are explained. In the examples, the compounds are identified by the Compound No. as in Tables 1 and 2, and "part(s)" represents "part(s) by weight".

Formulation Example 1

Fifty (50) parts of each of compounds 1-1 to 1-72 and 2-1 to 2-24, 3 parts of calcium ligninsulfonate, 2 parts of sodium lauryl sulfate, and 45 parts of synthetic hydrated silicondioxide are well pulverized and mixed, to separately obtain wettable powders of each compound.

Formulation Example 2

Ten (10) parts of each of compounds 1-1 to 1-72 and 2-1 to 2-24, 14 parts of polyoxyethylenestyryl phenyl ether, 6 parts of calcium dodecylbenzenesulfonate, 35 parts of xylene, and 35 parts of cyclohexanone are mixed to separately obtain emulsifiable concentrates of each compound.

Formulation Example 3

Two (2) parts of each of compounds 1-1 to 1-72 and 2-1 to 2-24, 2 parts of synthetic hydrated silica, 2 parts of calcium ligninsulfonate, 30 parts of bentonite, and 64 parts of kaolin clay are well pulverized and mixed. After adding water and well kneading, the mixtures are granulated and dried to separately obtain granules of each compound.

Formulation Example 4

Twenty-five (25) parts of each of compounds 1-1 to 1-72 and 2-1 to 2-24, 50 parts of a 10% aqueous solution of polyvinyl alcohol, and 25 parts of water are mixed, and are wet pulverized until the average particle diameter is 5 μm or less, to separately obtain flowables of each compound.

Formulation Example 5

Five (5) parts of each of compounds 1-1 to 1-72 and 2-1 to 2-24 is added into 40 parts of 10% aqueous solution of polyvinyl alcohol, and the mixture is emulsified and dispersed until the average diameter is 10 μm or less by homogenizer. Next, 55 parts of water is added to the resultant mixture to separately obtain concentrated emulsions of each compound.

Next, test examples are explained to show that the present compounds are effective as an active ingredient of a herbicide.

Test Example 1

Test for Foliar Treatment of Field

A cylindrical plastic pot having a diameter of 10 cm and a depth of 10 cm was filled with soil and then seeded with barnyardgrass, blackgrass, ivyleaf morningglory and velvetleaf These test plants were grown in a greenhouse for 14 days. Then, each of compounds 1-2, 1-3, 1-7, 1-19 and 1-28 was formulated into an emulsifiable concentrate according to Formulation Example 2 and then diluted to the prescribed amount with water containing a spreading agent and the dilution was uniformly sprayed over the foliage of the test plants with a sprayer at a rate of 1000 liters per hectare. After the application, the test plants were grown in the greenhouse for 16 days, and the herbicidal activity was determined. As a result, the growth of barnyardgrass, blackgrass, ivyleaf morningglory and velvetleaf were completely controlled when compounds 1-2, 1-3, 1-7, 1-19 and 1-28 were applied at the dosage of 125 g/ha, respectively.

Test Example 2

Test for Soil Surface Treatment of Field

A cylindrical plastic pot having a diameter of 10 cm and a depth of 10 cm was filled with soil and then seeded with barnyardgrass, blackgrass, ivyleaf morningglory and velvetleaf. Then, each of compounds 1-2, 1-3, 1-7, 1-19 and 1-28 was formulated into an emulsifiable concentrate according to Formulation Example 2 and then diluted to the prescribed amount with water, and the dilution was uniformly sprayed over the surface of the soil with a sprayer at a rate of 1000 liters per hectare. After the application, the test plants were grown in the greenhouse for 19 days, and the herbicidal activity was examined. The germination of barnyardgrass, blackgrass, ivyleaf morningglory and velvetleaf were completely controlled when compounds 1-2, 1-3, 1-7, 1-19 and 1-28 were applied at the dosage of 500 g/ha, respectively.

Test Example 3

Test for Foliar Treatment of Field

A cylindrical plastic pot having a diameter of 10 cm and a depth of 10 cm was filled with soil and then seeded with ivyleaf morningglory and blackgrass. These test plants were grown in a greenhouse for 10 days. Then, each of the test compounds was formulated into an emulsifiable concentrate according to Formulation Example 2 and then diluted to the prescribed amount with water containing a spreading agent and the dilution was uniformly sprayed over the foliage of the test plants with a sprayer at a rate of 1000 liters per hectare. After the application, the test plants were grown in the greenhouse for 16 days, and the herbicidal activity was examined.

The herbicidal activity was evaluated at 11 levels with indices of 0 to 10, i.e., designated by the numeral "0", "1", "2", "1", "3", "4", "5", "6", "7", "8", "9" or "10" wherein "0" means that there was no or little difference in the degree of germination or growth between the treated and the untreated tested plants at the time of examination, and "10" means that the test plants died completely or their germination or growth was completely inhibited. The results are shown in Table 3.

TABLE 3

| Test compound | Dosage (g/ha) | Herbicidal activity | |
|---|---|---|---|
| | | Ivyleaf morningglory | Blackgrass |
| 1–7 | 125 | 10 | 10 |
| | 32 | 10 | 6 |
| | 8 | 10 | 5 |
| Comparative compound A* | 125 | 10 | 6 |
| | 32 | 10 | 4 |
| | 8 | 7 | 3 |

*Comparative compound A

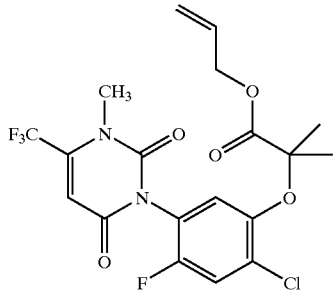

Test Example 4

Test for Soil Surface Treatment of Field

A plastic pot having an area of (26.5×19) cm² and a depth of 7 cm was filled with soil and then seeded with ivyleaf morningglory, velvetleaf, barnyardgrass and giant foxtail. Then, each of the test compounds was formulated into an emulsifiable concentrate according to Formulation Example 2 and then diluted to the prescribed amount with water, and the dilution was uniformly sprayed over the surface of the soil with a sprayer at a rate of 1000 liters per hectare. After the application, the test plants were grown in the greenhouse for 12 days, and the herbicidal activity was examined.

The herbicidal activity was evaluated by the same method as in Test Example 3. The results are shown in Table 4.

TABLE 4

| Test compound | Dosage (g/ha) | Herbicidal activity | | | |
|---|---|---|---|---|---|
| | | Ivyleaf morningglory | Velvet leaf | Barnyard grass | Giant foxtail |
| 1–7 | 500 | 10 | 10 | 10 | 10 |
| | 125 | 10 | 10 | 10 | 10 |
| | 32 | 2 | 10 | 6 | 10 |
| Comparative compound A | 500 | 8 | 10 | 10 | 10 |
| | 125 | 4 | 10 | 7 | 10 |
| | 32 | 0 | 3 | 1 | 4 |

By using the present compounds, excellent herbicidal effect can be obtained.

The invention being thus described, it will be apparent that the same way be varied in many ways. Such variations are within the spirit and scope of the invention, and all such modifications as would be apparent to one skilled in the art are intended to be included within the scope of the following claims.

What is claimed is:
1. An uracil compound represented by formula:

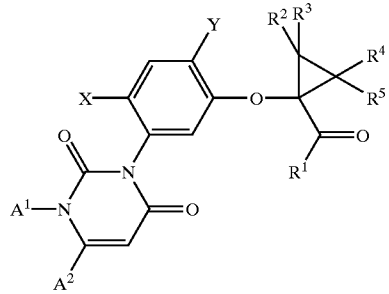

wherein
$A^1$ represents amino or $C_1$–$C_3$ alkyl, $A^2$ represents $C_1$–$C_3$ haloalkyl, X represents hydrogen or halogen, Y represents halogen, $R^1$ represents —$OR^{21}$—$ON(R^{22})R^{23}$, —$ON=C(R^{24})R^{25}$, —$SR^{26}$, —$N(R^{27})R^{28}$, —$N(R^{29})OR^{30}$, —$N(R^{31})SO_2R^{32}$ or —$N(R^{33})N(R^{34})R^{35}$, wherein $R^{21}$ represents hydrogen, $C_1$–$C_6$ alkyl, $C_1$–$C_6$ haloalkyl, $C_3$–$C_6$ alkenyl, $C_3$–$C_6$ alkynyl, $C_3$–$C_6$ cycloalkyl, carboxy $C_1$–$C_6$ alkyl, $C_1$–$C_6$ alkoxycarbonyl $C_1$–$C_6$ alkyl, $C_3$–$C_6$ alkenyloxycarbonyl $C_1$–$C_6$ alkyl, $C_3$–$C_6$ alkynyloxycarbonyl $C_1$–$C_6$ alkyl, $C_1$–$C_6$ alkoxy $C_1$–$C_6$ alkyl, benzyl or phenyl (the benzyl and phenyl may be substituted with one or more of halogen, $C_1$–$C_6$ alkyl and $C_1$–$C_6$ alkoxy) or tetrahydrofuryl (the tetrahydrofuryl may be substituted with one or more of hydroxy, $C_1$–$C_6$ alkoxy, $C_3$–$C_6$ alkenyloxy, $C_3$–$C_6$ alkynyloxy and $C_1$–$C_6$ alkylcarbonyloxy), $R^{22}$ and $R^{23}$ independently represent hydrogen, $C_1$–$C_6$ alkyl, $C_1$–$C_6$ haloalkyl, $C_3$–$C_6$ alkenyl, $C_3$–$C_6$ alkynyl or benzyl (the benzyl may be substituted with one or more of halogen, $C_1$–$C_6$ alkyl and $C_1$–$C_6$ alkoxy), $R^{24}$ and $R^{25}$ independently represent hydrogen, $C_1$–$C_6$ alkyl, $C_1$–$C_6$ haloalkyl, $C_3$–$C_6$ alkenyl, $C_3$–$C_6$ alkynyl, benzyl or phenyl (the benzyl and phenyl may be substituted with one or more of halogen, $C_1$–$C_6$ alkyl and $C_1$–$C_6$ alkoxy), $R^{26}$ represents hydrogen, $C_1$–$C_6$ alkyl, $C_1$–$C_6$ haloalkyl, $C_3$–$C_6$ alkenyl, $C_3$–$C_6$ alkynyl, $C_3$–$C_6$ cycloalkyl, carboxy $C_1$–$C_6$ alkyl, $C_1$–$C_6$ alkoxycarbonyl $C_1$–$C_6$ alkyl, $C_3$–$C_6$ alkenyloxycarbonyl $C_1$–$C_6$ alkyl, $C_3$–$C_6$ alkynyloxycarbonyl $C_1$–$C_6$ alkyl, $C_1$–$C_6$ alkoxy $C_1$–$C_6$ alkyl, benzyl or phenyl (the benzyl and phenyl maybe substituted with one or more of halogen, $C_1$–$C_6$ alkyl and $C_1$–$C_6$ alkoxy), $R^{27}$ represents hydrogen, $C_1$–$C_6$ alkyl, $C_1$–$C_6$ haloalkyl, $C_3$–$C_6$ alkenyl, $C_3$–$C_6$ alkynyl, $C_3$–$C_6$ cycloalkyl, carboxy $C_1$–$C_6$ alkyl, $C_1$–$C_6$ alkoxycarbonyl $C_1$–$C_6$ alkyl, $C_3$–$C_6$ alkenyloxycarbonyl $C_1$–$C_6$ alkyl, $C_3$–$C_6$ alkynyloxycarbonyl $C_1$–$C_6$ alkyl, $C_1$–$C_6$ alkoxy $C_1$–$C_6$ alkyl, benzyl or phenyl (the benzyl and phenyl may be substituted with one or more of halogen, $C_1$–$C_6$ alkyl and $C_1$–$C_6$ alkoxy), $R^{28}$ represents hydrogen, $C_1$–$C_6$ alkyl, $C_1$–$C_6$ haloalkyl, $C_3$–$C_6$ alkenyl, $C_3$–$C_6$ alkynyl, benzyl or phenyl (the benzyl and phenyl may be substituted with one or more of halogen, $C_1$–$C_6$ alkyl and $C_1$–$C_6$ alkoxy), $R^{29}$ and $R^{30}$ independently represent hydrogen, $C_1$–$C_6$ alkyl, $C_1$–$C_6$ haloalkyl, $C_3$–$C_6$ alkenyl, $C_3$–$C_6$ alkynyl or benzyl (the benzyl may be substituted with one or more of halogen, $C_1$–$C_6$ alkyl and $C_1$–$C_6$ alkoxy), $R^{31}$ represents hydrogen, $C_1$–$C_6$ alkyl, $C_1$–$C_6$ haloalkyl, $C_3$–$C_6$ alkenyl, $C_3$–$C_6$ alkynyl, benzyl or phenyl (the benzyl and phenyl may be substituted with one or more of halogen, $C_1$–$C_6$ alkyl and $C_1$–$C_6$ alkoxy), $R^{32}$ represents $C_1$–$C_6$ alkyl, $C_1$–$C_6$ haloalkyl, $C_3$–$C_6$ alkenyl, $C_3$–$C_6$ alkynyl, benzyl or phenyl (the benzyl and phenyl may be substituted with one or more of halogen, $C_1$–$C_6$ alkyl and $C_1$–$C_6$ alkoxy), $R^{33}$, $R^{34}$ and $R^{35}$ independently represent hydrogen, $C_1$–$C_6$ alkyl, $C_1$–$C_6$ haloalkyl, $C_3$–$C_6$ alkenyl, $C_3$–$C_6$ alkynyl, benzyl or phenyl (the benzyl and phenyl may be substituted with one or more of halogen, $C_1$–$C_6$ alkyl and $C_1$–$C_6$ alkoxy), $R^2$, $R^3$, $R^4$ and $R^5$ independently represent hydrogen or $C_1$–$C_3$ alkyl.

2. The uracil compound according to claim 1, wherein $R^2$, $R^3$, $R^4$ and $R^5$ are hydrogen.

3. The uracil compound according to claim 1, wherein X is fluorine and Y is chlorine.

4. The uracil compound according to claim 1, wherein $A^1$ is methyl and $A^2$ is trifluoromethyl.

5. The uracil compound according to claim 1, wherein $A^1$ is methyl, $A^2$ is trifluoromethyl, X is fluorine, Y is chlorine, and $R^2$, $R^3$, $R^4$ and $R^5$ are hydrogen.

6. The uracil compound according to claim 1, wherein $R^1$ is —$OR^{21}$, wherein $R^{21}$ is hydrogen, $C_1$–$C_6$ alkyl, $C_3$–$C_6$ alkenyl or $C_3$–$C_6$ alkynyl, or —$SR^{26}$, wherein $R^{26}$ is $C_1$–$C_6$ alkyl, $C_3$–$C_6$ alkenyl or $C_3$–$C_6$ alkynyl.

7. The uracil compound according to claim 1, wherein $A^1$ is methyl, $A^2$ is trifluoromethyl, X is fluorine, Y is chlorine, $R^1$ is —$OR^{21}$, wherein $R^{21}$ is hydrogen, $C_1$–$C_6$ alkyl, $C_3$–$C_6$ alkenyl or $C_3$–$C_6$ alkynyl, or —$SR^{26}$, wherein $R^{26}$ is $C_1$–$C_6$ alkyl, $C_3$–$C_6$ alkenyl or $C_3$–$C_6$ alkynyl, and $R^2$, $R^3$, $R^4$ and $R^5$ are hydrogen.

8. The uracil compound according to claim 1, wherein $R^1$ is —$OR^{21}$, wherein $R^{21}$ is $C_1$–$C_6$ alkyl.

9. The uracil compound according to claim 1, wherein $A^1$ is methyl, $A^2$ is trifluoromethyl, X is fluorine, Y is chlorine, $R^1$ is —$OR^{21}$, wherein $R^{21}$ is $C_1$–$C_6$ alkyl, and $R^2$, $R^3$, $R^4$ and $R^5$ are hydrogen.

10. An herbicidal composition comprising, as an active ingredient, the uracil compound according to claim 1, and inert carrier or diluent.

11. A method for controlling weeds which comprises applying a herbicidally effective amount of an uracil compound according to claim 1, to weeds or a place where weeds grow or will grow.

\* \* \* \* \*